(12) United States Patent
Ellingson et al.

(10) Patent No.: US 11,045,626 B2
(45) Date of Patent: Jun. 29, 2021

(54) GUIDE WIRE DEVICE AND METHOD

(71) Applicants: Andrew N. Ellingson, Bettendorf, IA (US); David I. Ellingson, Webster City, IA (US)

(72) Inventors: Andrew N. Ellingson, Bettendorf, IA (US); David I. Ellingson, Webster City, IA (US)

( * ) Notice: Subject to any disclaimer, the term of this patent is extended or adjusted under 35 U.S.C. 154(b) by 1155 days.

(21) Appl. No.: 15/448,299

(22) Filed: Mar. 2, 2017

(65) Prior Publication Data

US 2017/0252060 A1  Sep. 7, 2017

Related U.S. Application Data

(60) Provisional application No. 62/304,288, filed on Mar. 6, 2016.

(51) Int. Cl.
| | |
|---|---|
| A61B 34/20 | (2016.01) |
| A61M 25/01 | (2006.01) |
| A61M 25/09 | (2006.01) |
| A61B 90/00 | (2016.01) |
| A61B 10/04 | (2006.01) |

(52) U.S. Cl.
CPC ......... *A61M 25/0108* (2013.01); *A61B 34/20* (2016.02); *A61B 90/39* (2016.02); *A61M 25/0105* (2013.01); *A61M 25/09041* (2013.01); *A61B 2010/045* (2013.01); *A61B 2034/2063* (2016.02); *A61B 2090/062* (2016.02); *A61B 2090/067* (2016.02); *A61B 2090/3908* (2016.02); *A61B 2090/3929* (2016.02); *A61B 2090/3979* (2016.02); *A61B 2090/3995* (2016.02); *A61M 2025/0166* (2013.01); *A61M 2025/09116* (2013.01); *A61M 2025/09166* (2013.01)

(58) Field of Classification Search
None
See application file for complete search history.

(56) References Cited

U.S. PATENT DOCUMENTS

| | | | | |
|---|---|---|---|---|
| 5,409,004 | A | * | 4/1995 | Sloan ..................... A61B 6/502 600/434 |
| 6,081,741 | A | | 6/2000 | Hollis |
| 7,174,201 | B2 | * | 2/2007 | Govari ..................... A61B 5/06 382/124 |
| 7,444,178 | B2 | | 10/2008 | Goldbach |
| 7,747,307 | B2 | | 6/2010 | Wright |
| 8,412,311 | B2 | | 4/2013 | Kenneth |
| 8,452,375 | B2 | | 5/2013 | Krag |
| 8,892,185 | B2 | | 11/2014 | Sing |
| 2002/0145207 | A1 | * | 10/2002 | Anderson ......... H01L 23/49816 257/787 |
| 2003/0004411 | A1 | * | 1/2003 | Govari ................ A61B 17/1114 600/424 |
| 2003/0023161 | A1 | | 1/2003 | Govari |

(Continued)

*Primary Examiner* — Luther Behringer

(57) ABSTRACT

A guide wire deployment system that can be utilized as a pre-surgical procedure without the need for radiology imaging. The clip marker would include light and sonic sensors to determine angular orientation and distance from the needle. Wireless communication between the handheld insertion device and the clip marker would provide information to guide the needle to the clip marker location. The guide wire would then be pushed from the needle and laid in a path to outside the patient.

19 Claims, 30 Drawing Sheets

(56) References Cited

U.S. PATENT DOCUMENTS

| | | |
|---|---|---|
| 2004/0138555 A1 | 7/2004 | Krag |
| 2008/0021308 A1 | 1/2008 | Dimmer |
| 2008/0071170 A1* | 3/2008 | Kenneth ............... A61B 5/06 |
| | | 600/434 |
| 2008/0119726 A1 | 5/2008 | Immerz |
| 2008/0154125 A1 | 6/2008 | Maier |
| 2009/0018403 A1* | 1/2009 | Black ................ A61N 5/1048 |
| | | 600/300 |
| 2010/0160752 A1 | 6/2010 | Chance |
| 2010/0305430 A1 | 12/2010 | Troesken |
| 2013/0237912 A1 | 9/2013 | Speeg |
| 2013/0245493 A1 | 9/2013 | Hibner |
| 2013/0324803 A1* | 12/2013 | Mohajer ............ A61B 17/0469 |
| | | 600/249 |
| 2014/0309522 A1 | 10/2014 | Fullerton |
| 2015/0031989 A1 | 1/2015 | Whitmore |
| 2016/0175064 A1 | 6/2016 | Steilne |

* cited by examiner

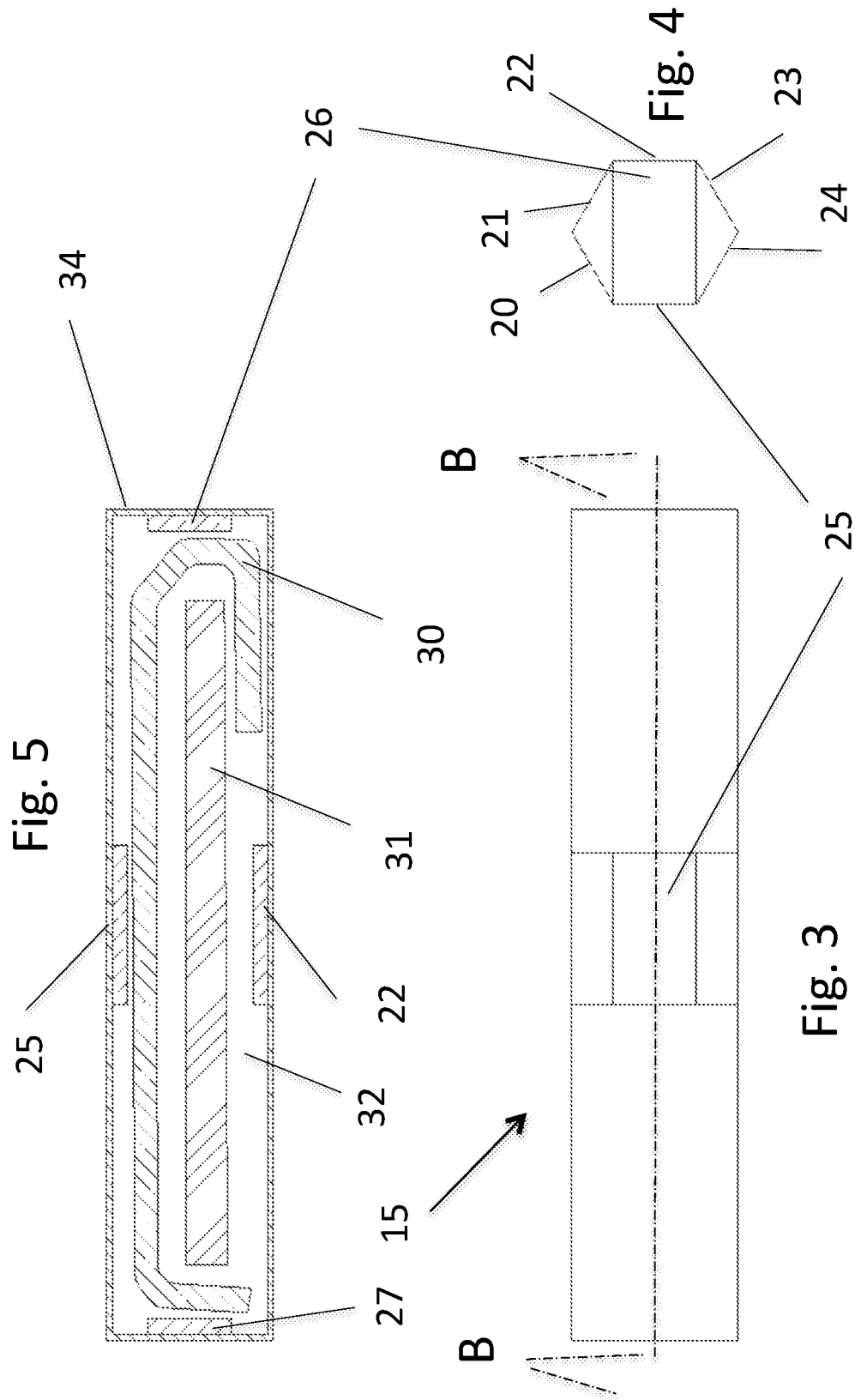

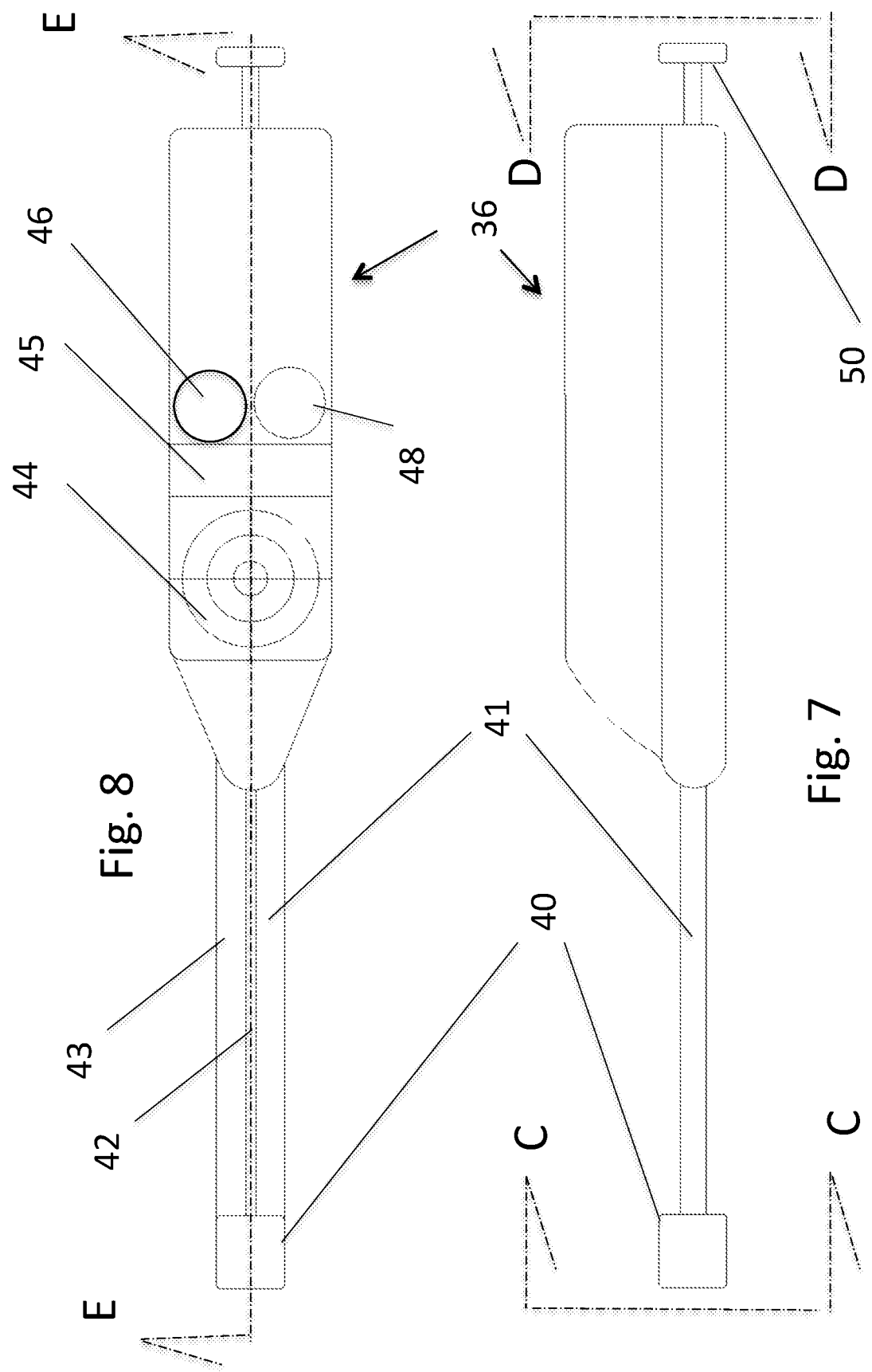

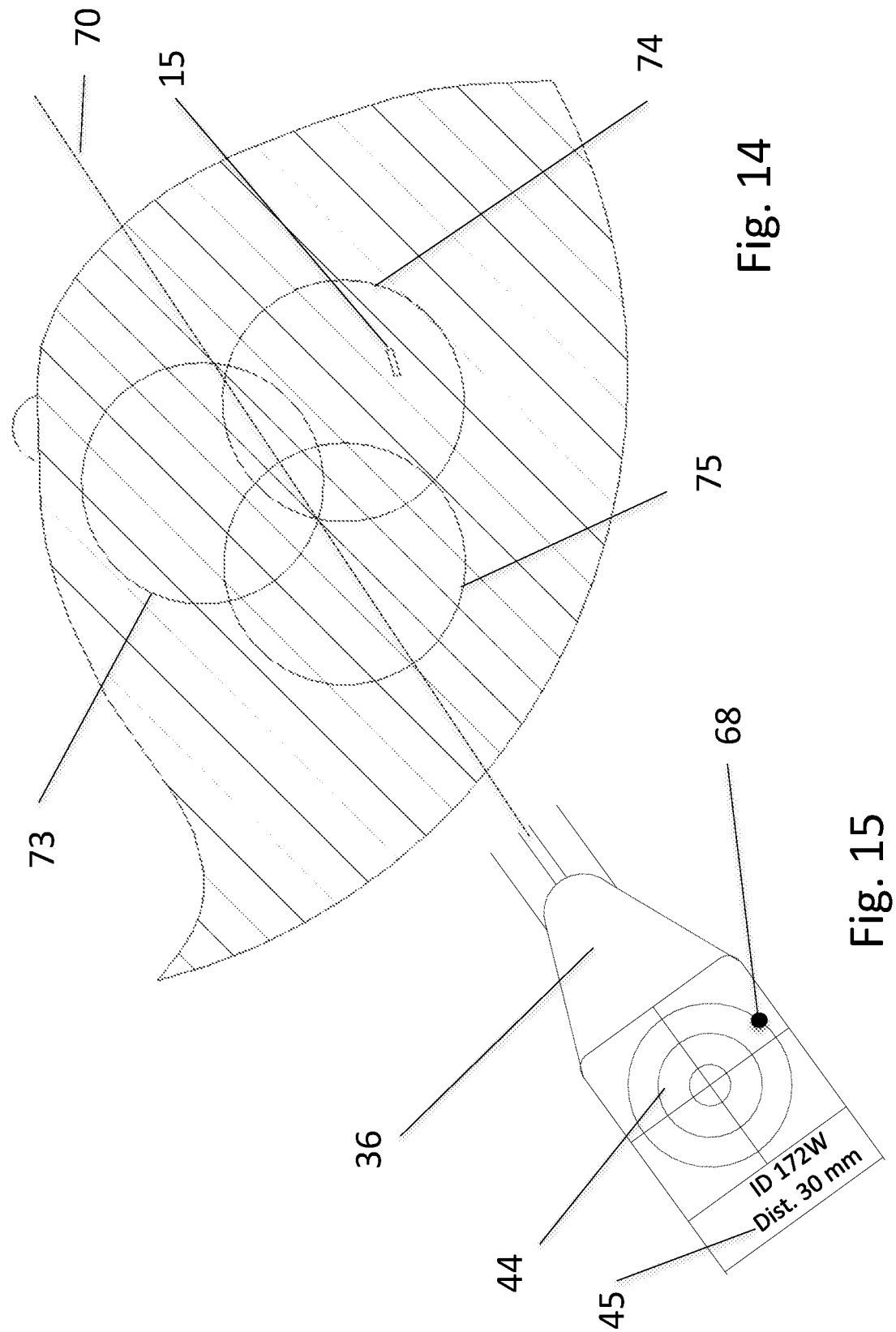

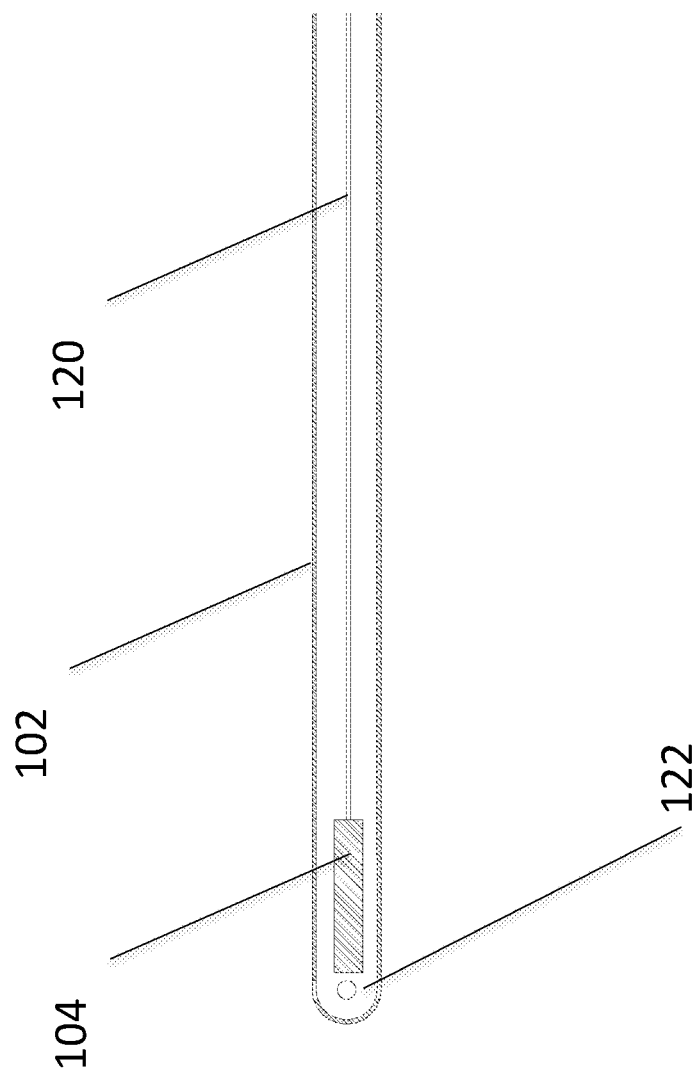

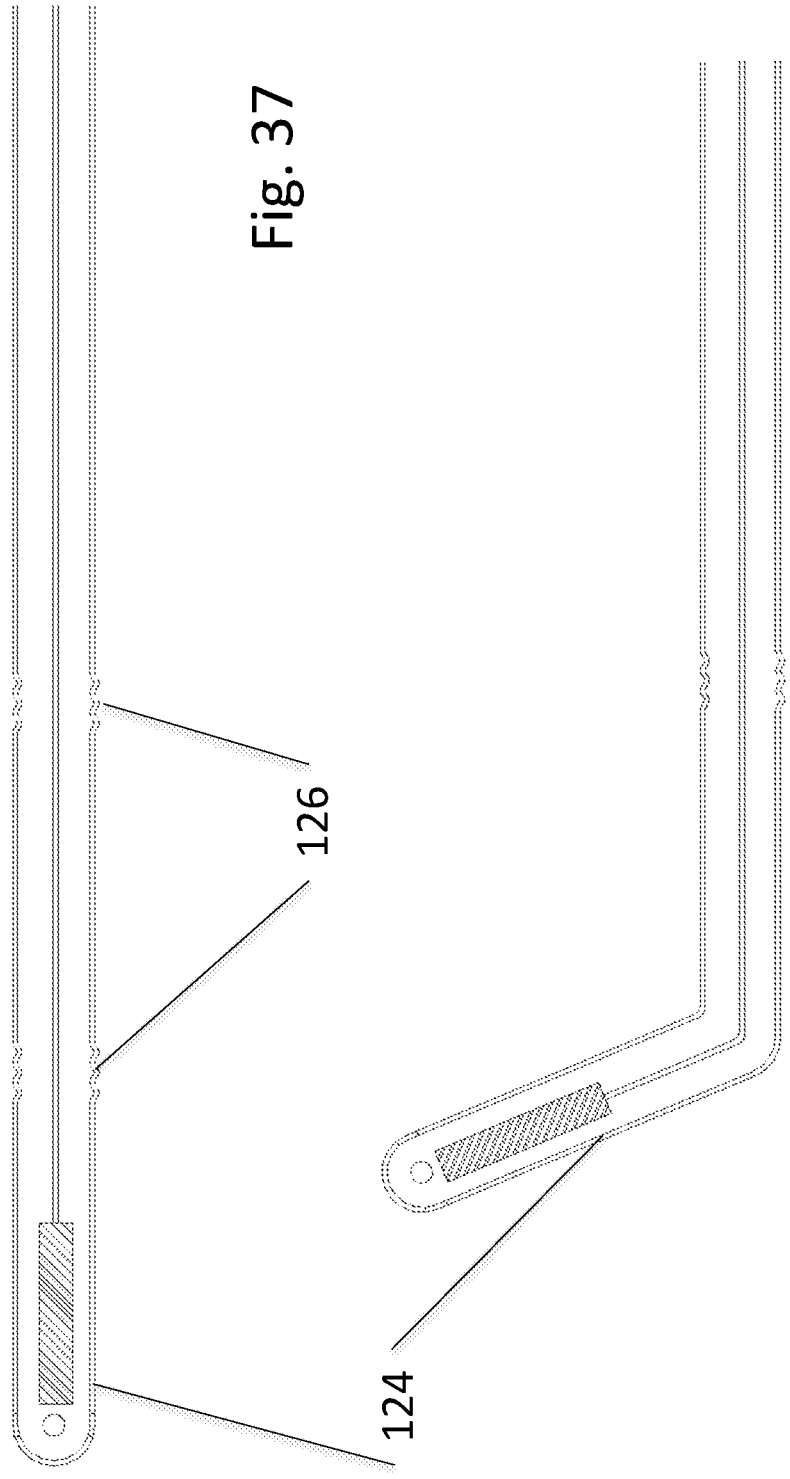

GUIDE WIRE DEVICE AND METHOD

CROSS-REFERENCE TO RELATED APPLICATIONS

This application claims priority to U.S. Provisional Patent Application Ser. No. 62/304,288 filed Mar. 6, 2016, titled "Guide Wire Device And Method", the entire contents of which is incorporated herein, both bodily and by reference.

FEDERALLY SPONSORED RESEARCH

Not Applicable

SEQUENCE LISTING OR PROGRAM

Not Applicable

FIELD OF THE INVENTION

The present invention relates to deploying a guide wire prior to a lumpectomy procedure.

BACKGROUND OF THE INVENTION

Biopsy samples have been obtained in a variety of ways with various medical devices. An example biopsy device is disclosed in U.S. Pub. No. 2013/0245493, entitled "Clutch and Valving System for Tetherless Biopsy Device", published Sep. 19, 2013.

Biopsy marker clips have been deployed in a variety of ways with various medical devices. An example marker clip deployment device is disclosed in U.S. Pub. No. 2013/0237912, entitled "Biopsy Marker Delivery Device", published Sep. 12, 2013.

The goal of the clip marker deployment is to place the clip marker as accurately as possible to the site where the tissue sample was removed. After the tissue sample is tested, it may be determined that a lumpectomy procedure is required.

The goal of the lumpectomy procedure is to remove a section of tissue with an adequate margin distance centered about the marker clip. To assist the surgeon, prior to the lumpetomy procedure, a guide wire is inserted into the breast. This guide wire insertion procedure is done in the radiology suite. Using multiple views, the radiologist positions the guide wire tip slightly past the clip marker. The tail of the guide wire exiting the breast is secured with tape and care must be taken to not disturb the guide wire prior to the lumpectomy procedure.

As an alternative to guide wire placement, some prior disclosures have outlined methods to determine the location of the clip marker directly. An example device is disclosed in U.S. Pub. No. 2014/0309522, entitled "Microwave Antenna Apparatus, Systems, and Methods for Localizing Markers or Tissue Structures Within a Body", published Oct. 16, 2014. Another device is disclosed in U.S. Pub. No. 2010/0305430, entitled "Tissue Marker", published Dec. 2, 2010. Another device is disclosed in U.S. Pub. No. 2008/0021308, entitled "Implantable Marker With a Leadless Signal Transmitter Compatible For Use In Magnetic Resonance Devices", published Jan. 24, 2008. Another device is disclosed in U.S. Pub. No. 2004/0138555, entitled "Systems and Methods For Locating and Defining a Target Location Within a Human Body", published Jul. 15, 2004.

Transmission of light through breast tissue is outlined in U.S. Pub. No. 2010/0160752, entitled "Detection, Imaging and Characterization of Breast Tumors", published Jun. 24, 2010.

The disclosure of each of the above-cited U.S. patents, U.S. patent application Publications, U.S. Provisional patent applications, and U.S. Non-Provisional patent application is incorporated by reference herein.

SUMMARY OF THE INVENTION

The present invention incorporates a smart clip marker with sensors and wireless transmission capability. This smart clip marker could be inserted in the same manner as outlined in U.S. Pub. No. 2013/0237912.

With this smart clip marker in place, the procedure step of having the guide wire inserted in the radiology suite could be eliminated. After normal pre-op, the patient could go directly to the surgical suite for the lumpectomy.

As a first step of the lumpectomy procedure, the surgeon would insert the guide wire using a wireless handheld insertion device. The wireless communication between the handheld insertion device and the smart clip marker would eliminate the need for any radiology imaging during the guide wire insertion. The surgeon would then proceed with the lumpectomy using the guide wire for localization to the marker clip position.

The directional guidance of the handheld insertion device would be accomplished with light sensing on the smart marker clip. Multiple light emitters on the handheld insertion device would provide both angular indication and magnitude of misalignment.

Distance from the handheld insertion device tip to the smart marker clip would be accomplished with an ultrasonic signal timing measurement. The smart marker clip would sense and transmit when the ultrasonic signal arrives. The amount of time for the signal to arrive would allow a marker clip distance to be calculated and displayed on the handheld insertion device.

The handheld device also has a probe to allow distance measurements to be taken during the lumpectomy procedure. These measurements provide better margin control during the procedure.

After the specimen has been removed, the handheld device with probe would be used to verify the clip marker is within the specimen. The correct margins around the clip marker would also be verified.

BRIEF DESCRIPTION OF THE DRAWINGS

FIG. 3 is a side view of a marker clip

FIG. 4 is an end view of a marker clip.

FIG. 5 is a section view of a marker clip taken along section line B-B from FIG. 3.

FIG. 7 is a side view of a deployment handheld.

FIG. 8 is a top view of a deployment handheld.

FIG. 14 is a section view of breast with wide light pattern taken along section line F-F from FIG. 13.

FIG. 15 is a close up top view of the off target display taken from FIG. 13.

FIG. 36 is a close up section view of the clip distance handheld tip taken along section line G-G from FIG. 35.

FIG. 37 is a close up section view of the clip distance handheld flexible tip.

FIG. 38 is a close up section view of the clip distance handheld flexible tip in a bent position.

Figure 1:
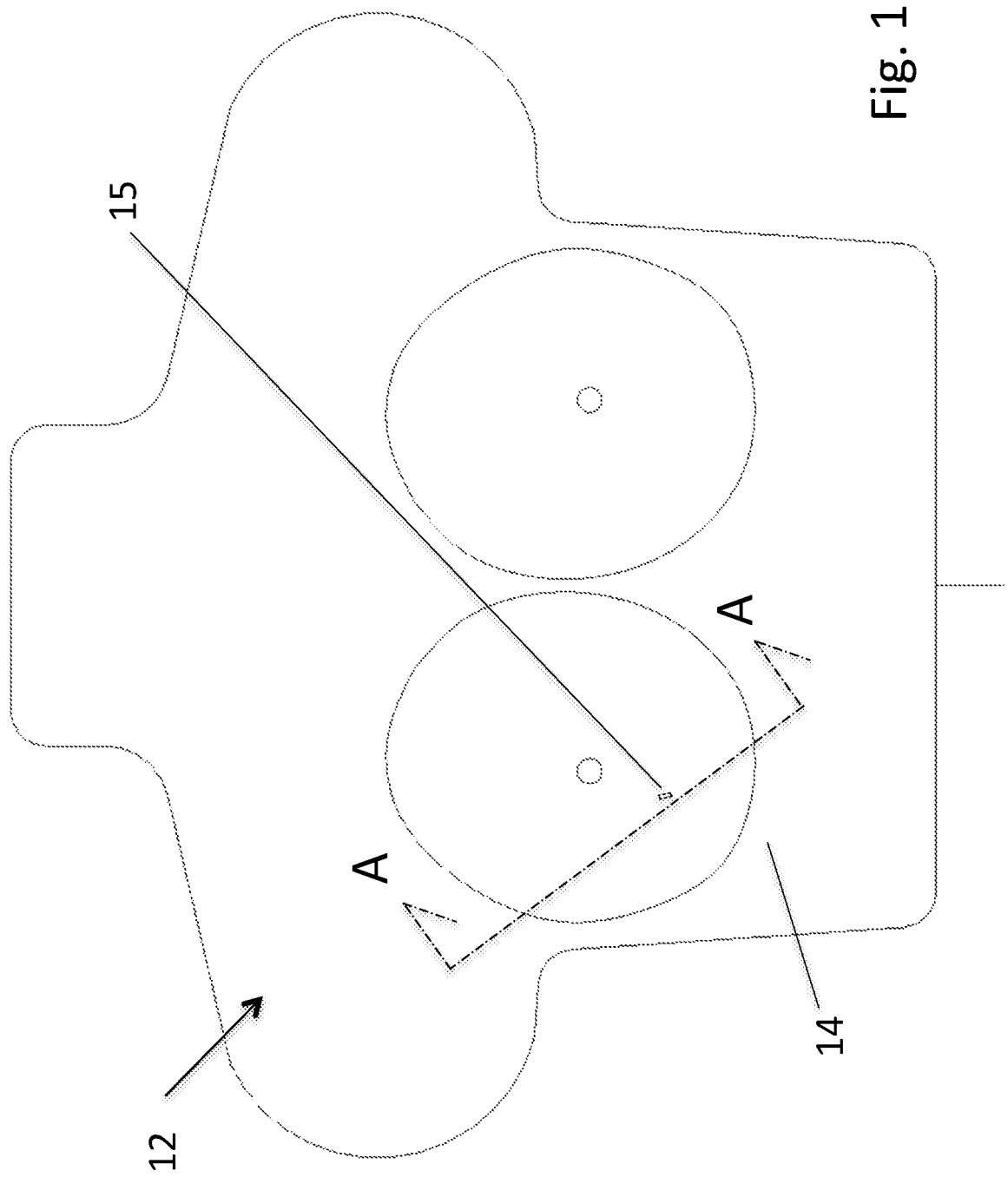
FIG. 1 is an AP (anterior posterior) view of a patient outline.

| REFERENCE NUMERALS | |
|---|---|
| 12 patient | 14 breast |
| 15 marker clip | 20 photocell A |
| 21 photocell B | 22 photocell C |
| 23 photocell D | 24 photocell E |
| 25 photocell F | 26 photocell G |
| 27 photocell H | 30 image bar |
| 31 micro components | 32 potting compound |
| 34 sealant | 36 deployment handheld |
| 40 holder | 41 left pushrod |
| 42 needle assembly | 43 right pushrod |
| 44 directional display | 45 character display |
| 46 user input | 48 pushrod release |
| 50 button spool | 53 LED A |
| 54 LED B | 55 LED C |
| 60 LED D | 61 LED E |

| REFERENCE NUMERALS | |
|---|---|
| 62 LED F | 64 upper handle |
| 65 deployment assembly | 66 wireless power emitter |
| 68 marker spot | 70 alignment line |
| 71 alignment line | 72 alignment line |
| 73 LED A shine outline | 74 LED B shine outline |
| 75 LED C shine outline | 77 holder ultrasonic |
| 78 LED D shine outline | 79 guide wire |
| 80 guide wire hook | 81 guide wire end |
| 82 light pipe G | 83 light pipe H |
| 84 LED E shine outline | 85 tip ultrasonic |
| 86 ultrasonic wire | 87 LED F shine outline |
| 88 needle | 89 light pipe I |
| 90 pushrod brake | 92 light pipe LED G |
| 93 light pipe LED H | 94 light pipe LED I |
| 95 needle end | 96 ultrasonic wire end |
| 98 button spool shoulder | 99 pushrod end |
| 101 clip distance assembly | 102 probe |
| 104 probe ultrasonic | 106 clip distance handheld |
| 110 extended button spool | 114 wire storage |
| 120 probe ultrasonic wire | 122 probe openings |
| 124 flexible probe | 126 flex joints |

DETAILED DESCRIPTION OF THE DRAWINGS

FIG. 1 is a an AP (anterior posterior) view of a patient outline. The patient 12 is supine. The marker clip 15 would have previously been placed in the breast 14. This view shows the X and Y position of the marker clip 15.

Figure 2:
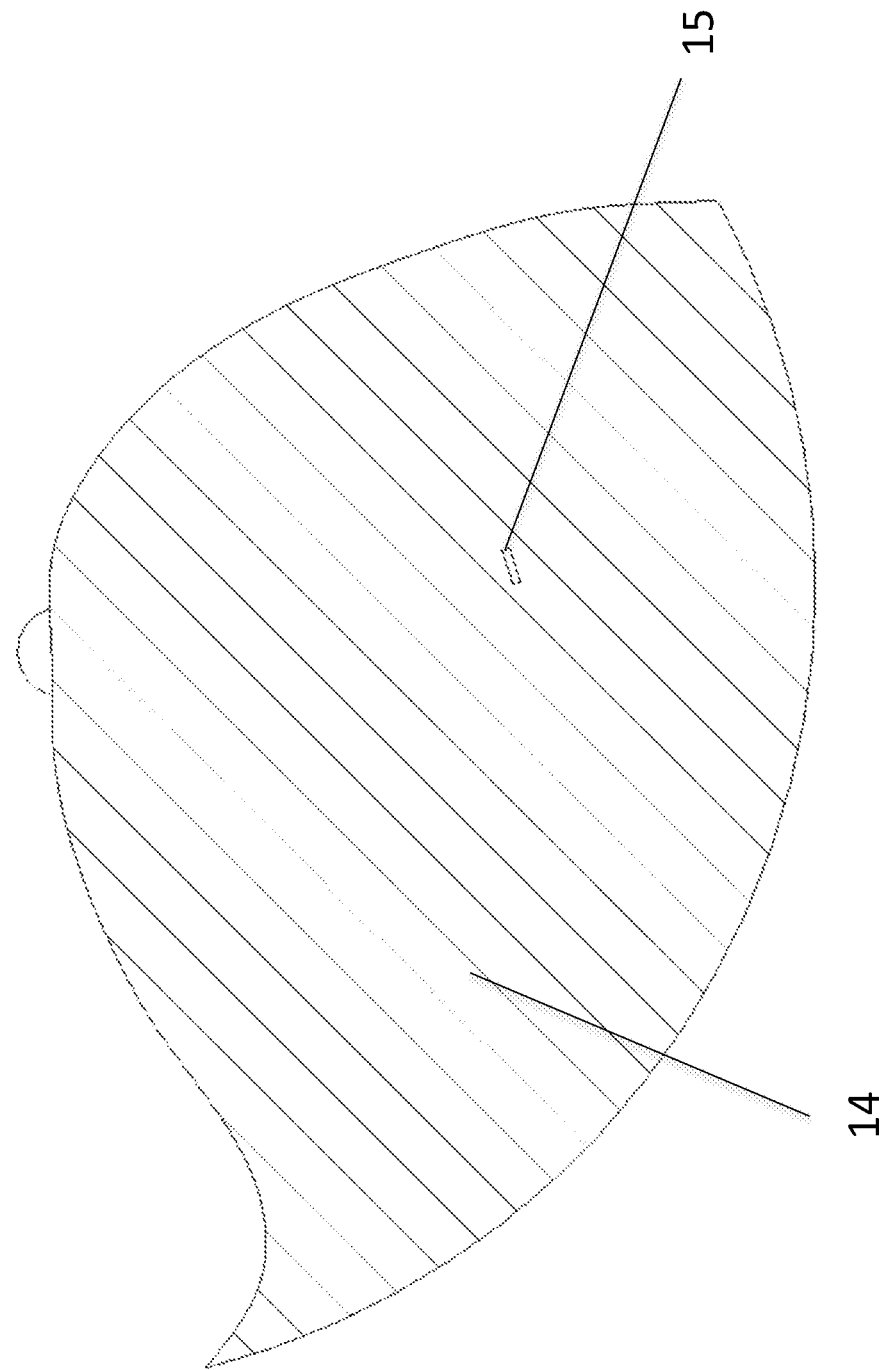
FIG. 2 is a section view of a breast taken along section line A-A from FIG. 1.

FIG. 2 is a section view of a breast taken along section line A-A from FIG. 1. This view shows the Z position of the marker clip 15.

FIG. 3 is a side view of a marker clip. The size of the marker clip 15 would be approximately 2 mm by 10 mm. When placed in the breast 14, the marker clip 15 would have pledgets attached to each end. Each pledget would be approximately 2 mm by ×10 mm. The purpose of the pledget is to improve the attachment of the marker clip 15 to surrounding tissue and resist movement of the marker clip 15 within the breast 14. The pledget would be constructed of a material that is translucent to light such as collagen. The pledget would also be constructed in a fibrous manner to provide pathways for light transmission. The pledget is not shown in any of the views of the marker clip 15.

The marker clip 15 has a hexagon shape. This is to provide six flat surfaces on the sides for placement of photo cells 20-25.

FIG. 4 is an end view of a marker clip. One end of the marker clip 15 includes photocell 26 and the other end photocell 27.

FIG. 5 is a section view of a marker clip taken along section line B-B from FIG. 3. The marker clip 15 includes an image bar 30 to facilitate location with existing imaging techniques such as x-ray or Mill. The image bar 30 material would be stainless steel or a similar imaging opaque material. Several shapes of the image bar 30 would be possible to allow multiple marker clips 15 to be individually identified. These shapes could include as shown in FIG. 3 and also an L or a U. Different lengths on the legs of the image bar 30 would provide more variations. The image bar 30 also provides a rigid structure for the marker clip 15. After the internal marker clip 15 components are in place, the potting compound 32 is added. The sealant 34 is then added to provide a clear nonpervious surface for the marker clip 15.

The micro components 31 include several devices. These devices would include the microprocessor, ultrasonic sensor, wireless power receiver, radio frequency transmitter/receiver, and the capacitor power supply. If possible, it would be desirable from a cost point of view for all these devices to be surface mounted on a circuit board. This circuit board would be placed in the marker clip 15 in the position shown as micro components 31. Discrete lead wires would then be attached from the circuit board to each of the photocells.

Space constraints may not permit a circuit board to be used. In this event, a discrete silicon die cut of the microprocessor will be used. Each of the other devices will be discrete silicon die cuts or micro components. Individual gold lead wires will be welded from die to device. For space reasons, it may be necessary for the microprocessor die cut to be rectangular in shape. An example die size may be 1 mm by 4 mm. A custom microprocessor mask with circuits in this rectangular shape would allow this.

Figure 6:
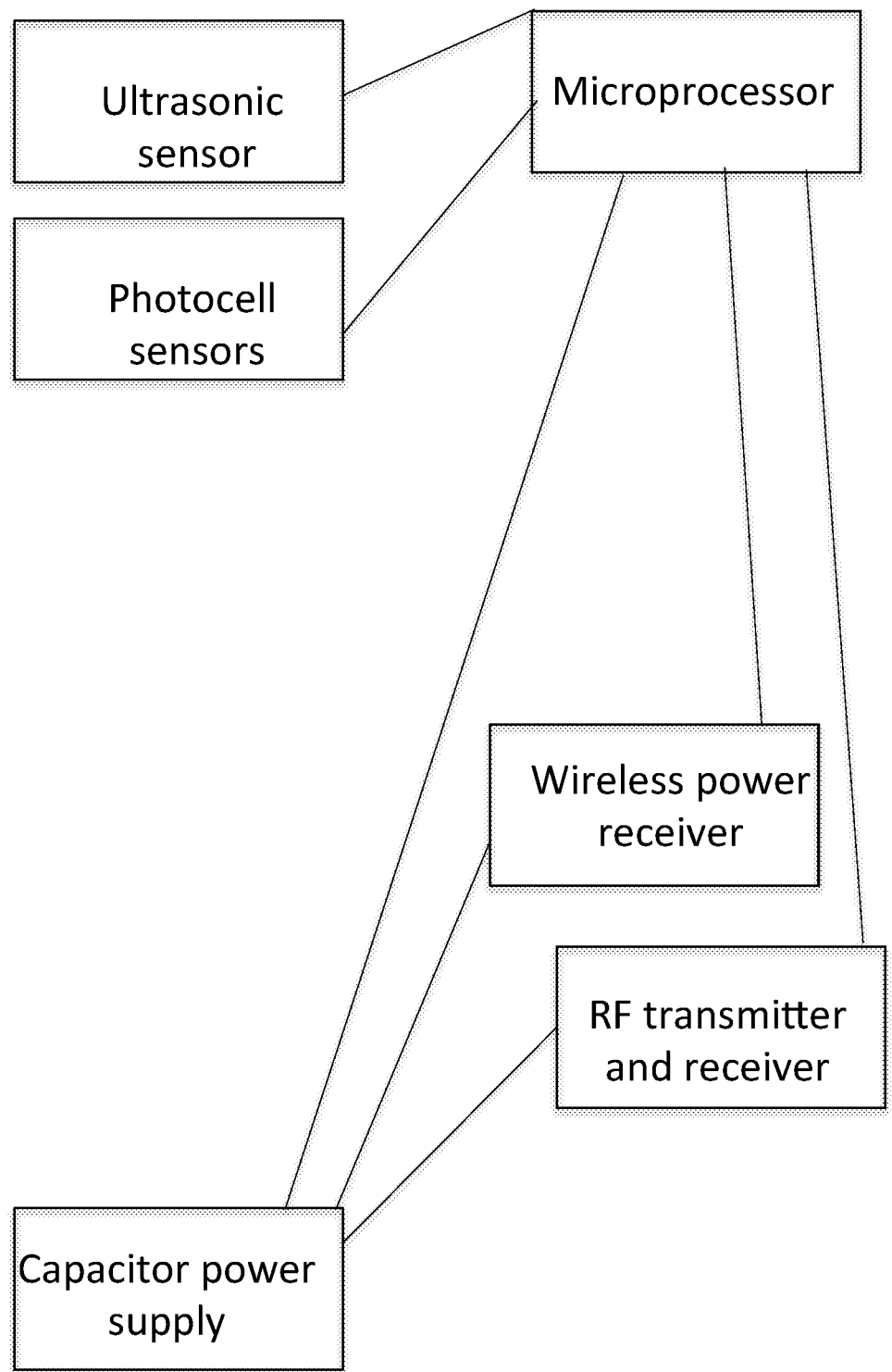
FIG. 6 is a block diagram of the marker clip electronic components.

FIG. 6 is a block diagram of the marker clip electronic components. A wireless power emitter 66 is part of the deployment handheld 36. The wireless power receiver is tuned to the emitter 66 frequency. The capacitor power supply regulates the voltage and smooths any short term power interruptions. The ultrasonic sensor could be a piezoelectric device or capacitive micromachined ultrasonic transducer (CMUT). Although ultrasonic would be preferred, an audio range sound sensor could be utilized. If an audio range sound sensor was utilized, the holder ultrasonic 77 would be replaced with a holder audio range emitter. Also the probe ultrasonic 104 would be replaced with a probe audio range emitter. For the purposes of the claims of this application, the term sonic shall inclusively refer to ultrasonic and audio range.

The radio frequency (RF) transmitter and receiver provide the capability for the marker clip to digitally communicate with the deployment handheld 36.

The photocell sensors could be photodiodes operating in photovoltaic mode. The key parameter is high sensitivity.

FIG. 7 is a side view of a deployment handheld. The deployment handheld 36 includes a holder 40 which is fixed to the left pushrod 41 and the right pushrod 43. At the rear of the deployment handheld 36 is the button spool 50 which is used to deploy the guide wire 79.

FIG. 8 is a top view of a deployment handheld. This view shows the pushrods 41, 43 and the needle assembly 42. The needle assembly 42 does not move relative to the deployment handheld 36. The holder 40 and pushrods 41,42 can move toward the deployment handheld 36 when the pushrod release 48 is depressed.

The directional display 44 is used to show the relative alignment of the needle assembly 42 to the marker clip 15 position. The character display 45 is used to indicate the identification number of the marker clip 15 and distance from the guide wire 79 to the marker clip 15.

The user input 46 is to allow the operator to select from the character display. It could include up/down inputs with rocking action and select input with push action.

Figure 9:
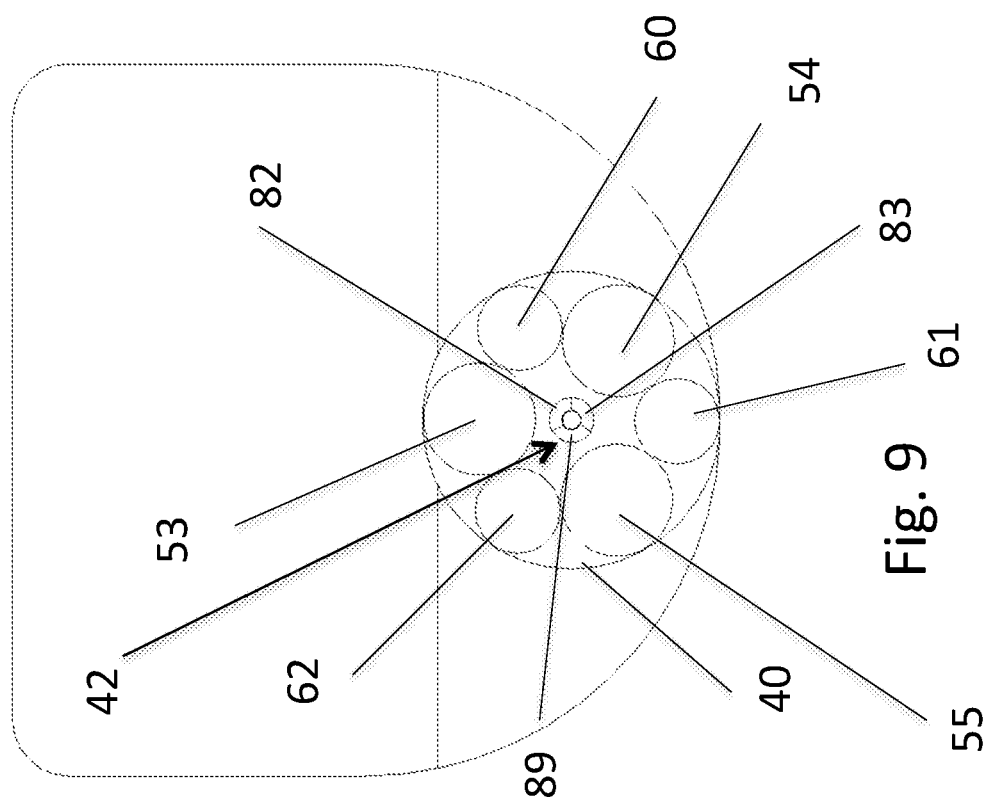
FIG. 9 is a enlarged end view of the deployment handheld taken from view line C-C from FIG. 7.

FIG. 9 is an enlarged end view of the deployment handheld taken from view line C-C from FIG. 7. In this view the needle assembly 42 is visible from an opening in the holder 40. Six LEDs (light-emitting diode) 53-62 are shown. These LEDs are used to transmit light through the breast 14 tissue. The near infrared (NIR) window for breast tissue transmission is 626 to 1316 nm. An LED light wavelength of 730 nm is optimal for this transmission. Although LEDs have been identified, alternate constructions of light emitters would provide function to the apparatus. Other types of light emitters include incandescent bulb, gas-discharge lamp and laser.

LED A 53, LED B 54 and LED C 55 are the wide angle light transmitters. These LEDs would have a power of 1000 mW and total beam angle of 25 degrees.

LED D 60, LED E 61 and LED F 62 are the narrow angle light transmitters. These LEDS would have a power of 500 mW and total beam angle of 10 degrees. These power ratings are constant duty and normal life. Due to this application having short duty cycle and limited life requirement, the LEDs could be overpowered by a factor of two or more.

Figure 10:
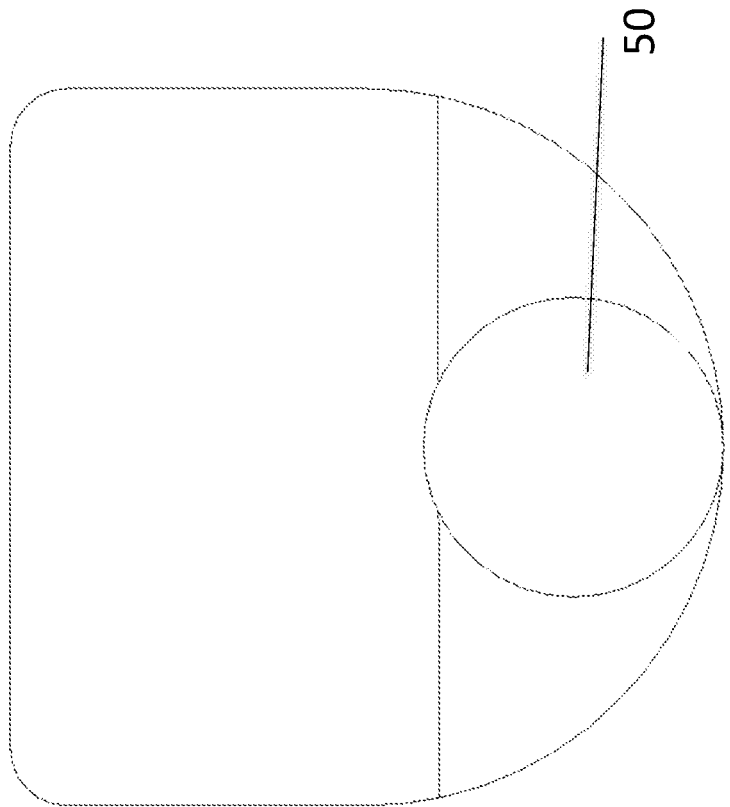
FIG. 10 is a enlarged end view of the deployment handheld taken from view line D-D from FIG. 7.

FIG. 10 is a enlarged end view of the deployment handheld taken from view line D-D from FIG. 7. This end view shows the position of the button spool 50.

Figure 11:
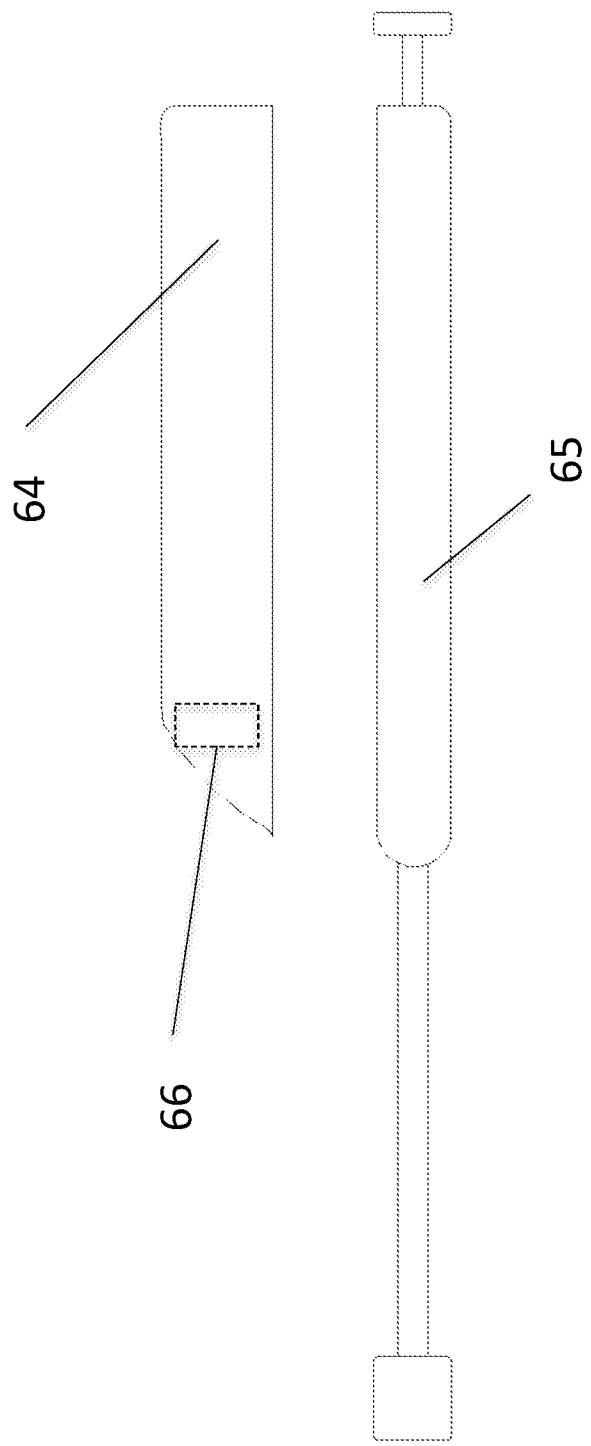
FIG. 11 is a side view of a separated deployment handheld.

FIG. 11 is a side view of a separated deployment handheld. The deployment handheld 36 is a combination of two devices. All patient contact is limited to the deployment assembly 65 which is a disposable device. As much as possible, the high cost electronics are included in the upper handle 64 which is reusable.

The upper handle 64 and the deployment assembly 65 would be easily connected with a snap fit. This connection would include any needed electrical and mechanical contact points.

The wireless power emitter 66 is shown as part of the upper handle 64. The wireless power transmission system would use near field inductive coupling.

Figure 12:
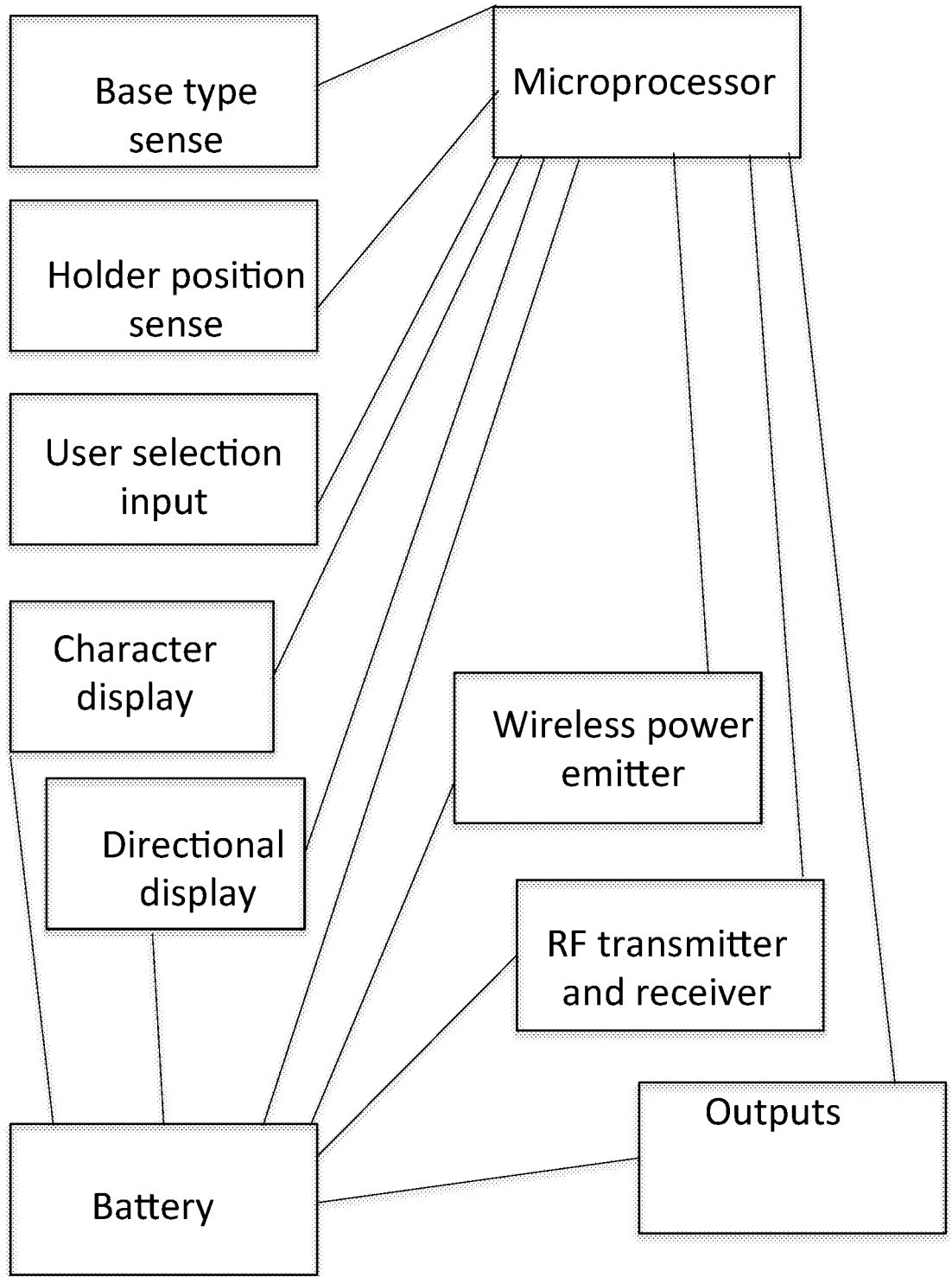
FIG. 12 is a block diagram of the deployment handheld electronic components.

FIG. 12 is a block diagram of a deployment handheld electronic components. The base type sense and holder 40 position sense would be electrical signals coming from the deployment assembly 65. These signals would cross from the deployment assembly 65 to the upper handle 64 via electrical contacts. The base type sense would communicate that a deployment assembly 65 is attached to the upper handle 64. The deployment assembly 65 would include a sensor for holder 40 position.

Figure 13:
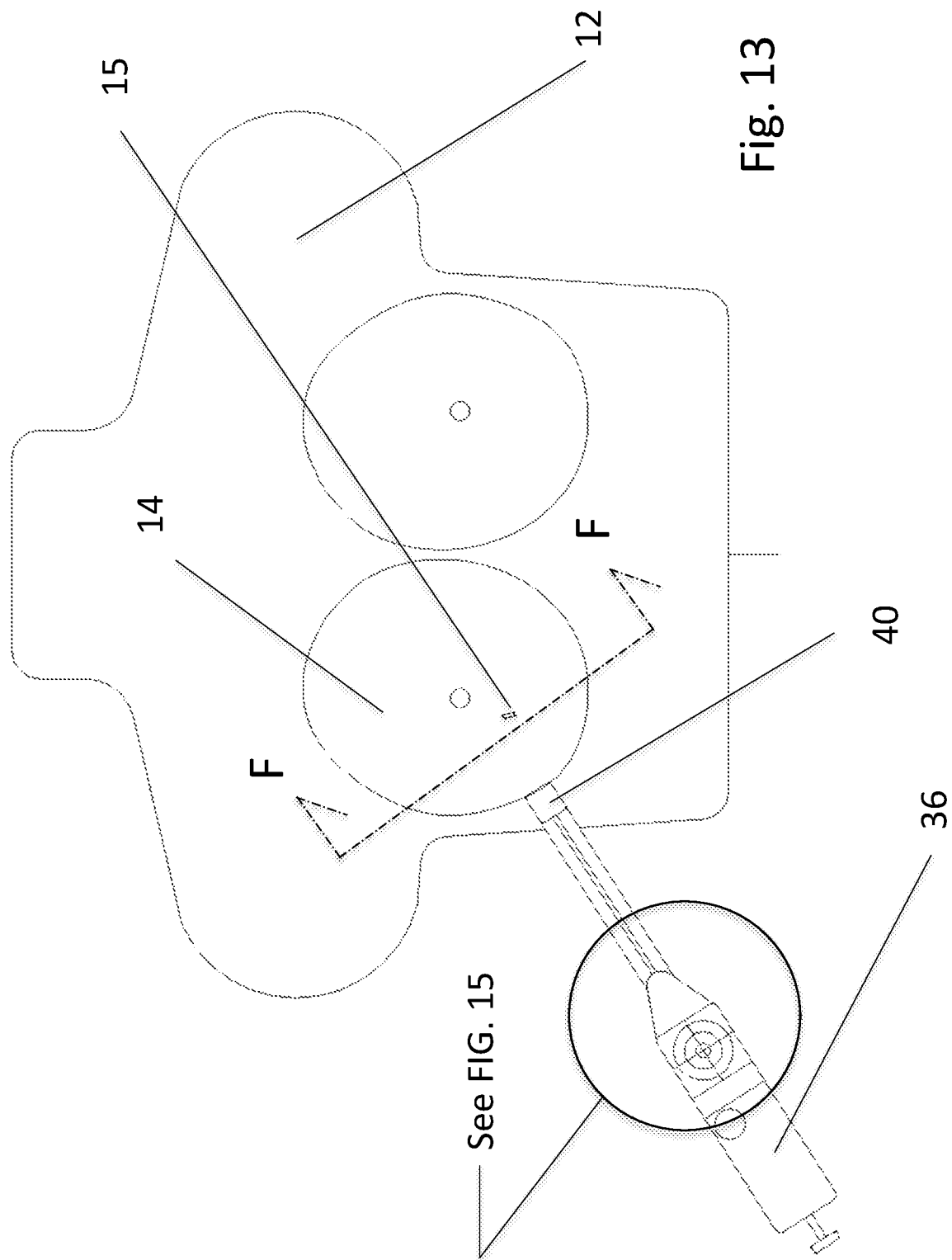
FIG. 13 is an AP view of a patient outline with a deployment handheld in position.

FIG. 13 is an AP view of a patient outline with a deployment handheld in position. Following are the initial steps of the guide wire placement procedure— a. The surgeon would know the approximate location of the marker clip 15 from past imaging history. An example description would be lower outer quadrant right breast, approximately 6 to 7 o'clock position.

b. The surgeon would know the ID number of the desired marker clip 15.

c. The surgeon would activate the deployment handheld 36, verify it passes self-test, and hold the deployment handheld 36 near the breast 14.

d. The deployment handheld 36 would perform a search for any responding marker clips 15 within transmitting range. The deployment handheld 36 would activate the wireless power emitter. Any marker clips 15 within range would receive this signal, wakeup the marker clip 15 power supply, and begin RF transmission of the ID number.

e. Multiple marker clip 15 IDs may be found. There may be multiple marker clips 15 in the breast 14, in the other patient 12 breast, or potentially other staff in the proximity.

f. All identified marker clip 15 IDs would be shown on the character display 45. The surgeon would use the user input 46 to select the correct marker clip 15. The correct marker clip 15 and the deployment handheld 36 are now paired.

g. The surgeon would orient the axis of the deployment handheld and place the holder 40 against the breast 14 as estimated from past imaging history. A slight compression of the breast 14 tissue with the holder 40 is desirable. This slight compression (approximately 5 mm) will improve the light transmission through the breast 14 tissue and the ultrasonic transmission through the holder 40 to breast 14 interface surface.

h. The deployment handheld 36 would provide information to the surgeon on distance and angular alignment to the marker clip 15.

i. The surgeon would repeat step (g) and step (h) until the optimal holder 40 position and alignment are identified. The optimal position is the shortest distance with good alignment.

FIG. 14 is a section view of breast with wide light pattern taken along section line F-F from FIG. 13. Following are the steps of the deployment handheld 36 alignment procedure— a. The deployment handheld 36 has been paired with the marker clip 15.

b. The holder 40 has been placed at the optimum position on the breast 14. The breast 14 tissue has been slightly compressed by the holder 40.

c. LED A 53 is energized and a signal is sent to the marker clip 15 that LED A 53 has been energized. The light from LED A 53 would impact the section of breast 14 as shown in LED A shine outline 73. This shine outline would not impinge on the marker clip 15. None of the photocells on the marker clip would have sensed light and a signal would be sent to the deployment handheld. After receipt of this signal, LED A 53 would be de-energized.

d. LED B 54 is energized and a signal is sent to the marker clip 15 that LED B 54 has been energized. The light from LED B 54 would impact the section of breast 14 as shown in LED B shine outline 74. This shine outline would impinge on the marker clip 15. One or more of the photocells on the marker clip would have sensed light and a signal would be sent to the deployment handheld. After receipt of this signal, LED B 54 would be de-energized.

e. LED C 55 is energized and a signal is sent to the marker clip 15 that LED C 55 has been energized. The light from LED C 55 would impact the section of breast 14 as shown in LED C shine outline 75. This shine outline would not impinge on the marker clip 15. None of the photocells on the marker clip would have sensed light and a signal would be sent to the deployment handheld 36. After receipt of this signal, LED C 55 would be de-energized.

f. The holder ultrasonic 77 would be energized with a pulse and a signal sent to the marker clip that the holder ultrasonic 77 has been energized. The marker clip 77 would record a precise time interval from receipt of the RF signal that the holder ultrasonic 77 has been energized until the marker clip 15 ultrasonic sensor provides a sense input signal. This time interval would be sent to the deployment handheld 36. The deployment handheld 36 would convert this information to distance in mm. The RF signal would have essentially zero travel time from deployment handheld 36 to the marker clip 15. The ultrasonic pulse would travel through breast 14 tissue at approximately 1.5 mm per microsecond. For the example shown (approx. 30 mm), the time interval recorded by the marker clip 15 would be approx. 45 microseconds.

g. Steps c thru f would complete one marker clip 15 scan. The data from this scan would be updated on the deployment handheld 36 displays as shown in FIG. 15. The total scan time for steps c thru f would be approximately 100 milliseconds. The deployment handheld 36 displays would be updated 10 times per second.

A portion of the LED light shined through the breast 14 tissue is absorbed and scattered. The LED shine outline includes the scattered light that is within the photocell sensitivity range.

FIG. 15 is a close up top view of the off target display taken from FIG. 13. FIG. 15 shows the display per the FIG. 14 light outlines. The alignment line 70 shows the alignment of the deployment device 36 from FIG. 15 projected on to FIG. 14. The marker clip 15 ID number is shown in the character display 45. The distance from the tip ultrasonic 85 to the marker clip 15 is shown in the character display 45.

The marker spot 68 shows the magnitude and angular orientation of the deployment handheld 36 misalignment relative to the marker clip 15. Because LED B shine outline 74 was the only response, the marker spot 68 is indicated as shown just inside the $3^{rd}$ circle and in the angular direction of the LED B shine outline 74.

Figure 16:
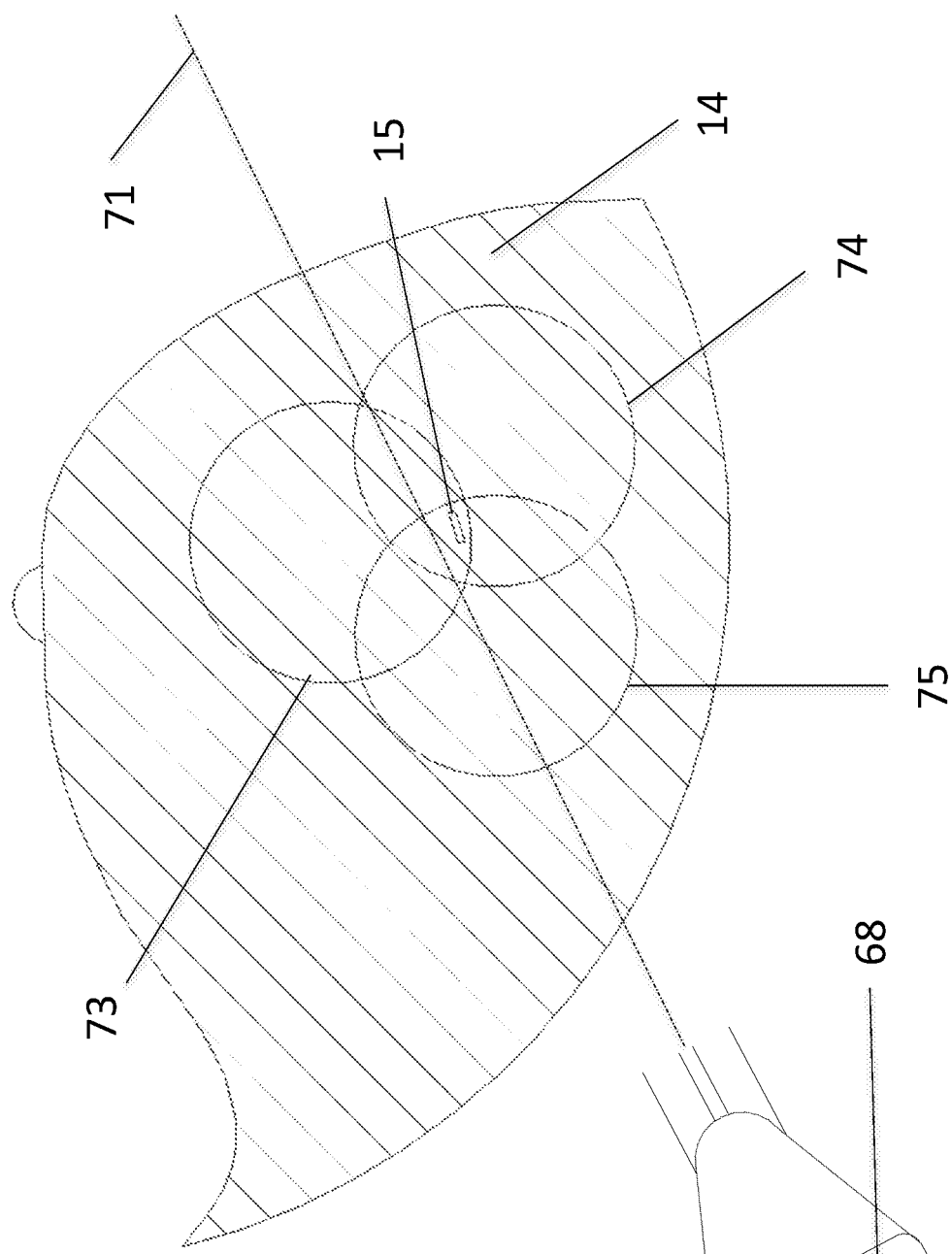
FIG. 16 is a section view of a breast with on target wide light pattern.

FIG. 16 is a section view of a breast with on target wide light pattern. After the surgeon views the FIG. 15 display, the surgeon adjusts the deployment handheld 36 alignment resulting in the FIG. 16 light pattern. For this scan, all three LED outlines 73-75 are sensed by the marker clip 15.

Figure 17:
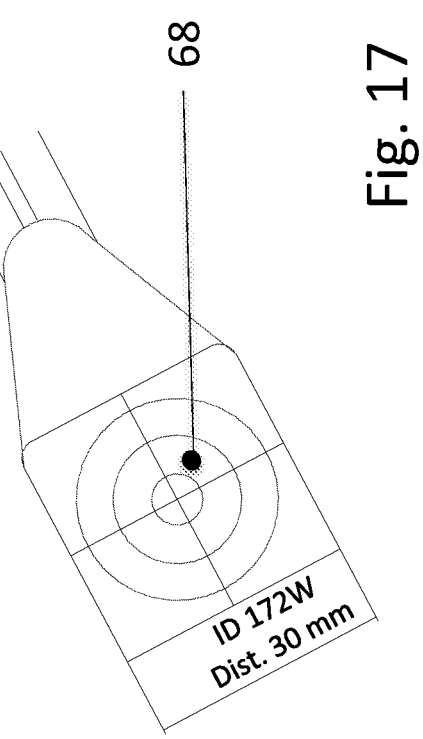
FIG. 17 is a close up top view of the approaching target display.

FIG. 17 is a close up top view of the approaching target display. FIG. 17 shows the display per the FIG. 16 light outlines. The alignment line 71 shows the alignment of the deployment device 36 from FIG. 17 projected on to FIG. 16. Because all three LED outlines 73-75 are sensed, the handheld device 36 now switches to the narrow light pattern of LEDs 60-62. An LED energizing sequence similar to LEDs 53-55 is now employed for LEDs 60-62. As a result, only LED D 60 was sensed by the marker clip 15. Because LED D shine outline 78 was the only response, the marker spot 68 is indicated as shown just inside the $2^{rd}$ circle and in the angular direction of the LED D shine outline 78.

Figure 18:
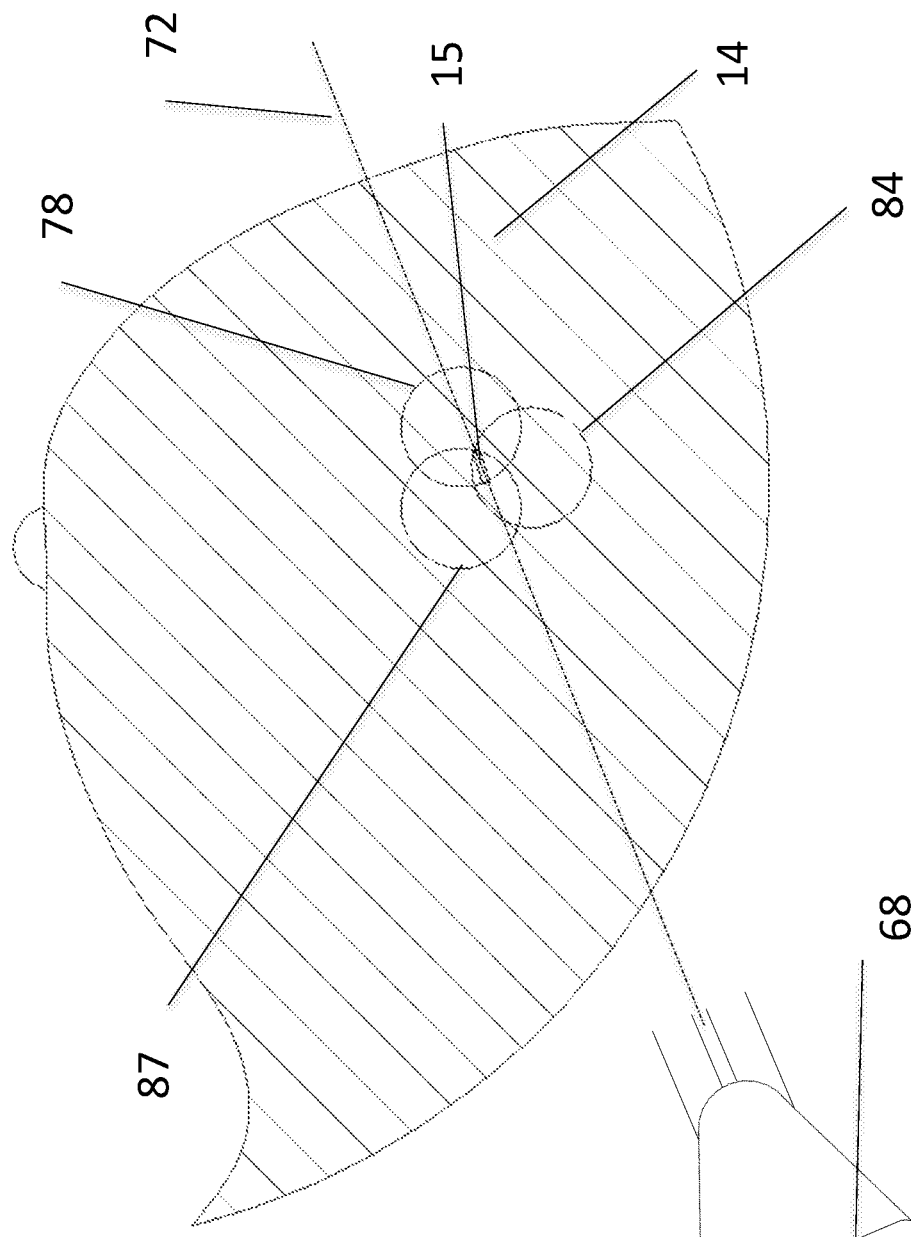
FIG. 18 is a section view of a breast with on target narrow light pattern.

FIG. 18 is a section view of a breast with on target narrow light pattern. After the surgeon views the FIG. 17 display, the surgeon adjusts the deployment handheld 36 alignment resulting in the FIG. 18 light pattern. For this scan, all three LED outlines 78, 84 and 87 are sensed by the marker clip 15.

Figure 19:
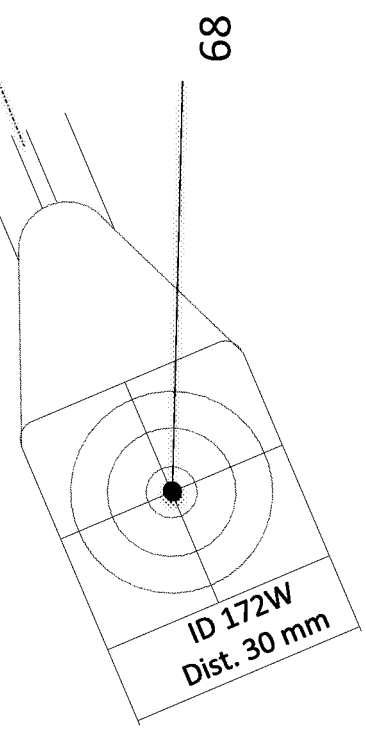
FIG. 19 is a close up top view of the on target display.

FIG. 19 is a close up top view of the on target display. FIG. 19 shows the display per the FIG. 18 light outlines. The alignment line 72 shows the alignment of the deployment device 36 from FIG. 19 projected on to FIG. 18. Because all three LED outlines 78, 84 and 87 are sensed by the marker clip, the marker spot 68 is indicated as shown inside the $1^{st}$ circle. The handheld device 36 is now properly aligned and ready for needle assembly 42 insertion into the breast 14.

Figure 20:
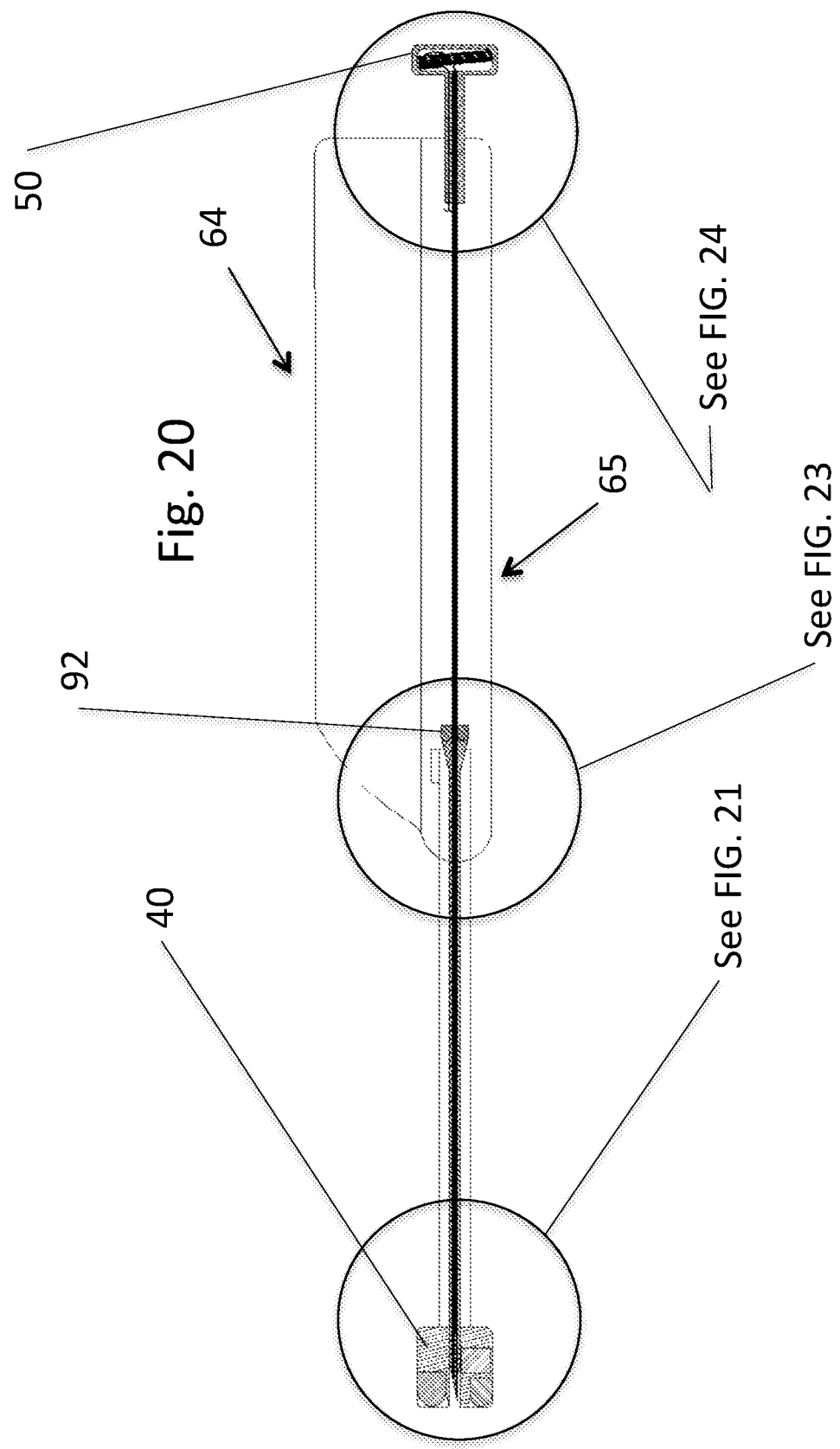
FIG. 20 is a section view of the deployment handheld taken along section line E-E from FIG. 8.

FIG. 20 is a section view of the deployment handheld taken along section line E-E from FIG. 8. Shown in this view are the holder 40, light pipe LED G 92, and button spool 50. Note that some parts such as the upper handle 64 and the deployment assembly 65 are shown only in outline rather than cross section.

Figure 21:
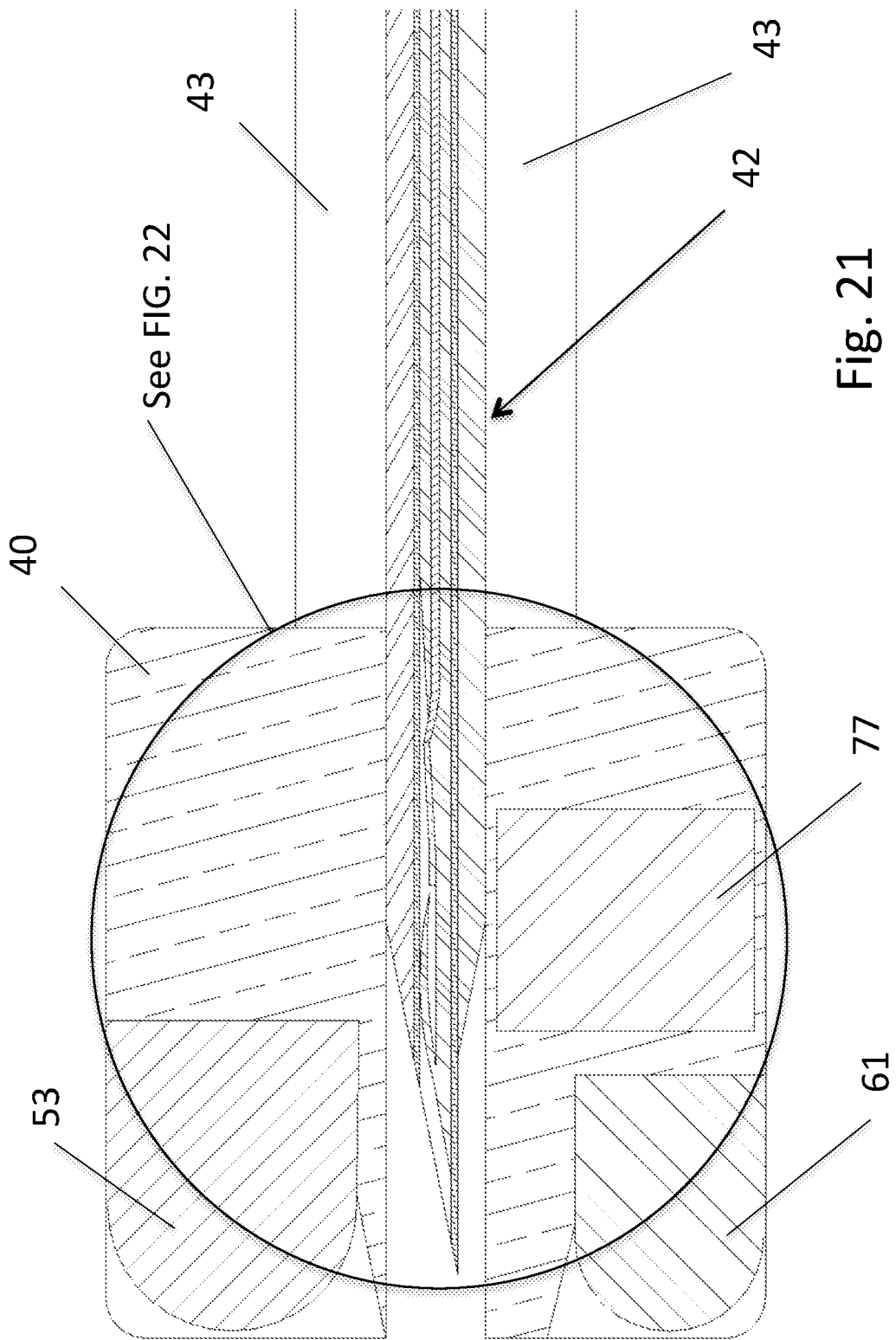
FIG. 21 is a close up section view of the holder taken from FIG. 20.

FIG. 21 is a close up section view of the holder taken from FIG. 20. Shown in this view are LED A 53 and LED E 61. Also shown is the right pushrod 43 and needle assembly 42. The holder ultrasonic 77 could be a piezoelectric or speaker device and is mounted inside the holder 40. The purpose of the holder ultrasonic 77 is to transmit an ultrasonic pulse to the breast 14. Since the holder 40 is pressed against the breast 14, the surface to surface transmission loss will be small. If needed, air holes could be located within the holder 40 from the holder ultrasonic 77 to the breast 14 contact surface.

All of the wiring for the holder 40 would route through the right pushrod 43. After exiting the end of the right pushrod 43, extra wire and space would be provided to allow the right pushrod 43 to retract into the deployment assembly 65.

Figure 22:
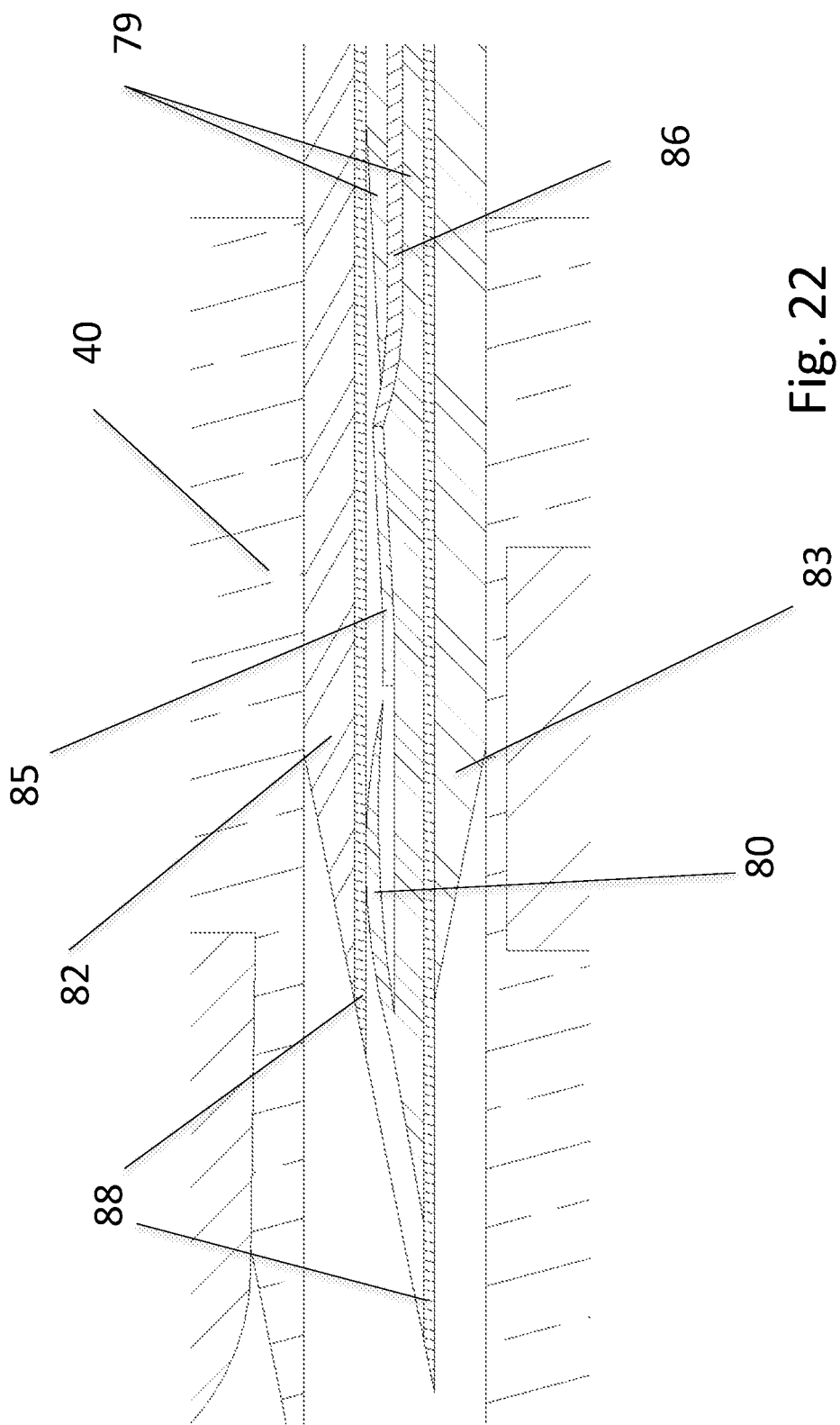
FIG. 22 is a close up section view of the needle tip taken from FIG. 21.

FIG. 22 is a close up section view of the needle tip taken from FIG. 21. The needle assembly 42 includes the needle 88, light pipes 82,83 and 89, and guide wire 79. The needle 88 is made from stainless steel and is sharp to facilite insertion into the breast 14. Surrounding the needle 88 are light pipes 82, 83 and 89. These light pipes are shown in end view in FIG. 9.

Light pipes 82, 83 and 89 could be incorporated as either of two purposes:
a. They could be used to further the deployment handheld 36 alignment accuracy by providing a further narrowing of the light pattern.
b. They could be used as an alternate construction rather than LEDs 60-62.

Inside the needle 88 is the guide wire 79. The guide wire 79 is made from a metallic alloy material and is sharp to facilite insertion into the breast 14. The guide wire hook 80 is shown in the stored position.

The tip ultrasonic 85 is a piezoelectric device attached to the guide wire 79. The purpose of the tip ultrasonic 85 is to provide greater accuracy for distance to the marker clip 15 rather than the holder ultrasonic 77. The tip ultrasonic 85 would not be enabled until the needle 88 has been inserted into the breast 14. Due to the limited power of the tip ultrasonic 85, the marker clip 15 would only be able to sense this device at short range. When the marker clip 15 is receiving a signal from the tip ultrasonic 86, the deployment handheld 36 would ignore the holder ultrasonic 77 signal, and instead display distance utilizing the tip ultrasonic 86.

The ultrasonic wire 86 is a two conductor insulated wire that is positioned inside the guide wire 79. The two conductors would be attached to the tip ultrasonic 85.

As an alternate construction, the ultrasonic wire 86 could be a single conductor insulated wire if the guide wire 79 was made from an electrically conductive material such as a metallic alloy. In this case, the guide wire 79 would be the second conductor. The tip ultrasonic 85 would be electrically connected to the guide wire 79 and the ultrasonic wire 86.

Figure 23:
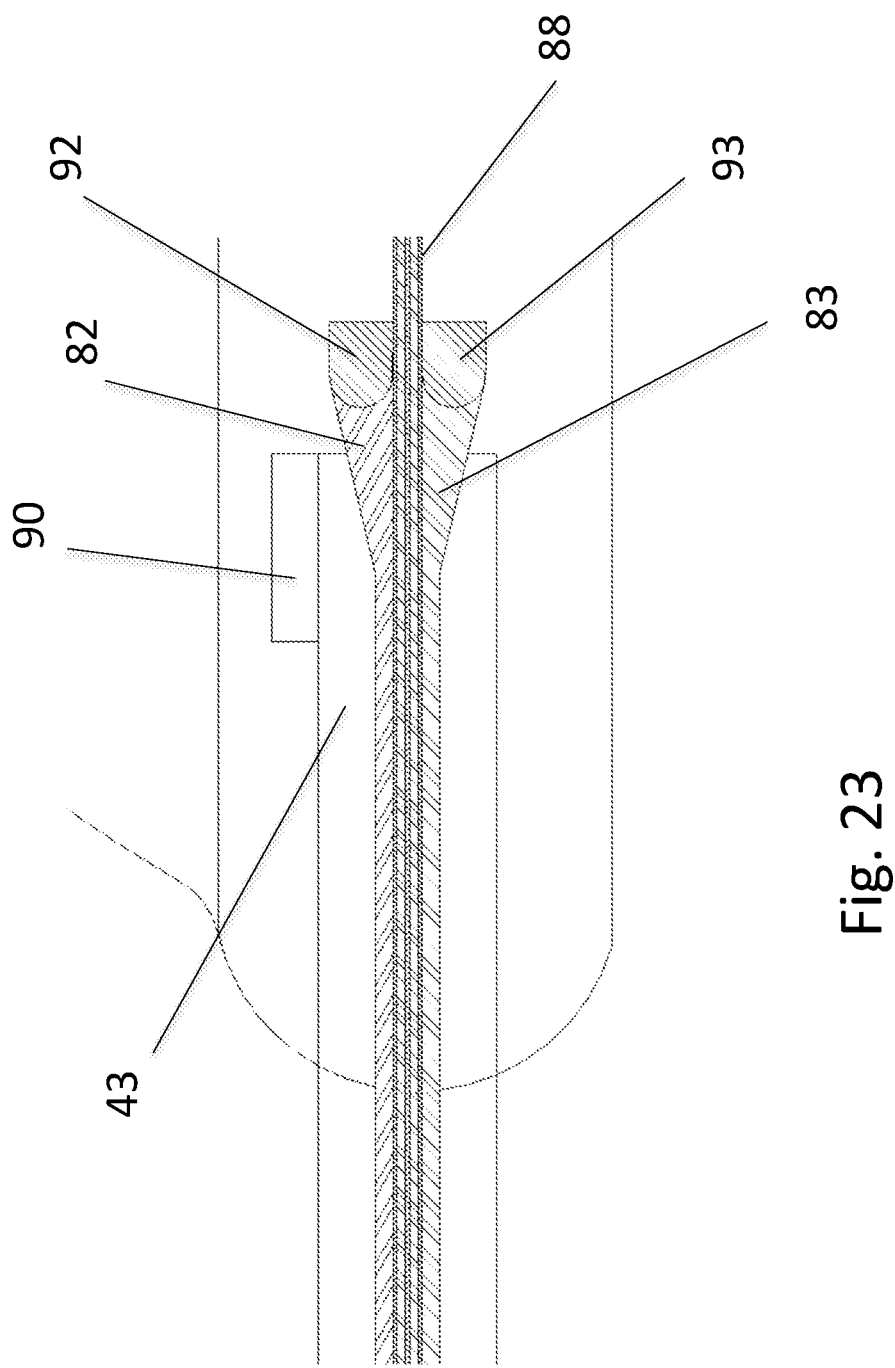
FIG. 23 is a close up section view of the light pipe taken from FIG. 20.

FIG. 23 is a close up section view of the light pipe taken from FIG. 20. Light pipe LED G 92 is shown in position to shine into light pipe G 82. The other two light pipes would utilize similar LED shine construction.

The pushrod brake 90 is shown adjacent the right pushrod 43. The holder 40 and pushrods 41,43 retract into the deployment assembly 65. The pushrod brake 90 in the engaged position as shown resist this movement. When the pushrod release 48 button as shown in FIG. 8 is depressed by the surgeon, the pushrod brake 90 moves to the release position and the holder 40 is free to move. This actuation between the pushrod release 48 and the pushrod brake 90 would cross the gap between the upper handle 64 and the deployment assembly 65 as a mechanical linkage.

Figure 24:
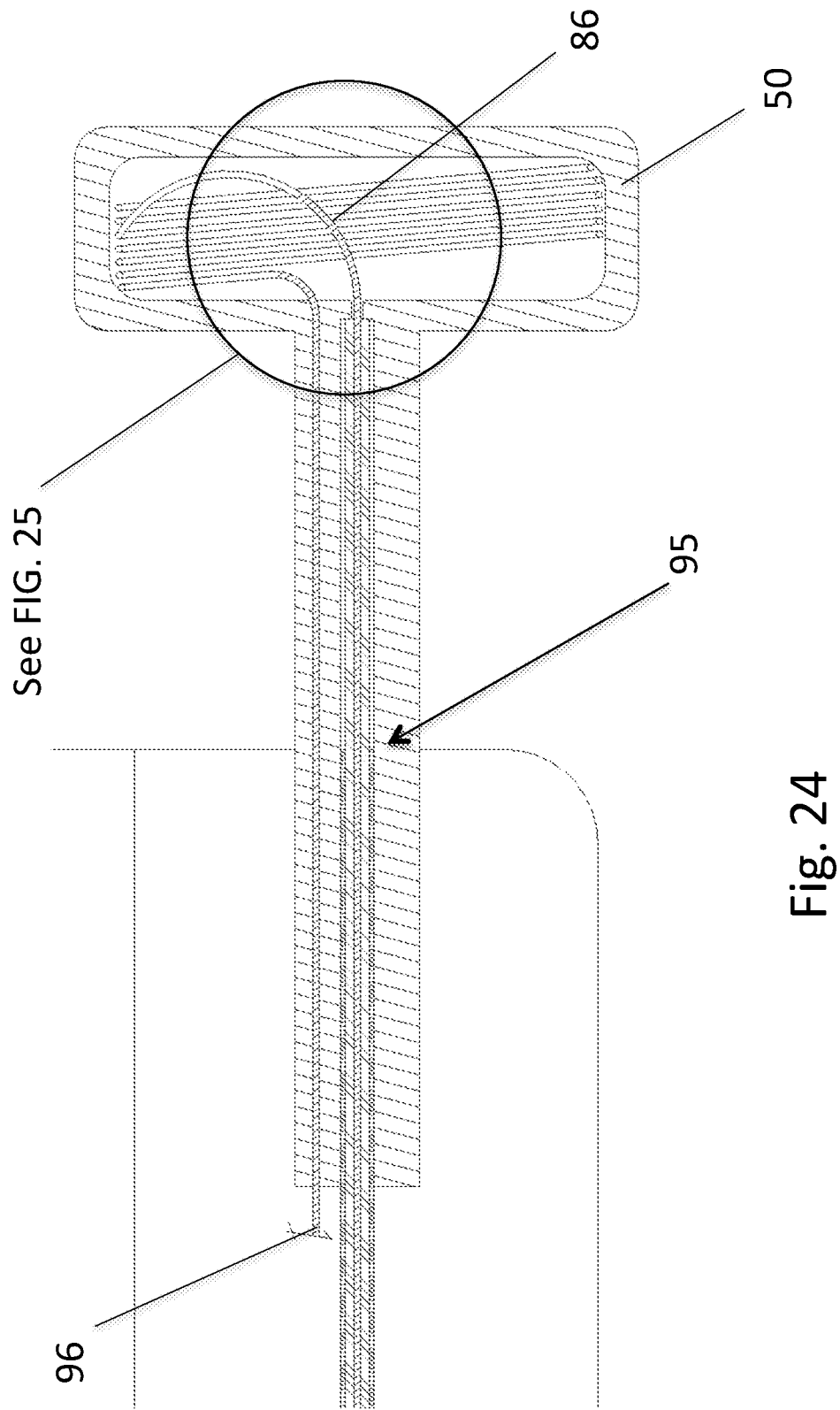
FIG. 24 is a close up section view of the button spool taken from FIG. 20.

FIG. 24 is a close up section view of the button spool taken from FIG. 20. After the needle 88 has been fully inserted into the breast the proper distance, the surgeon would depress the button spool 50 to insert the guide wire 79 into the breast 14. Note the needle end 95 of the needle 88.

The ultrasonic wire end 96 would have extra wire and space to allow button spool 50 travel.

Figure 25:
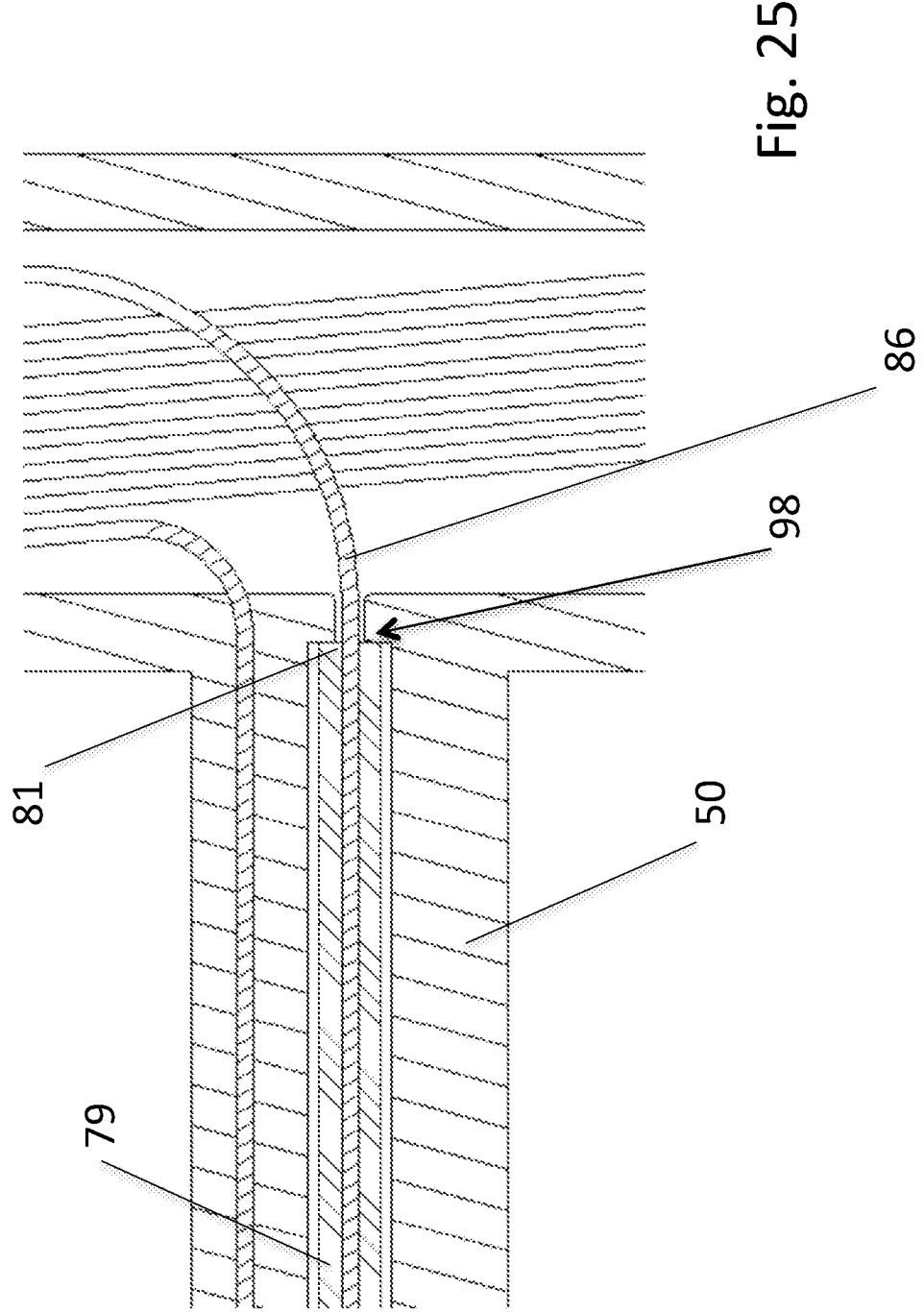
FIG. 25 is a close up section view of the spool wire taken from FIG. 24.

FIG. 25 is a close up section view of the spool wire taken from FIG. 24. The guide wire end 81 abuts the button spool shoulder 98. This provides the forcing surface to move the guide wire 79 forward when the button spool 50 is depressed.

Note the clearance hole at the button spool shoulder 98 for the ultrasonic wire 86. After the button spool 50 has been depressed, the guide wire hook 80 engages the breast 14 tissue. As the deployment handheld 36 is retracted, the guide wire 79 is pulled out. This clearance hole allows the ultrasonic wire 86 to play out into the needle 88. A sufficient length of ultrasonic wire 86 is stored in the button spool 50 to allow the guide wire 79 to exit the needle 88 tip.

Figure 26:
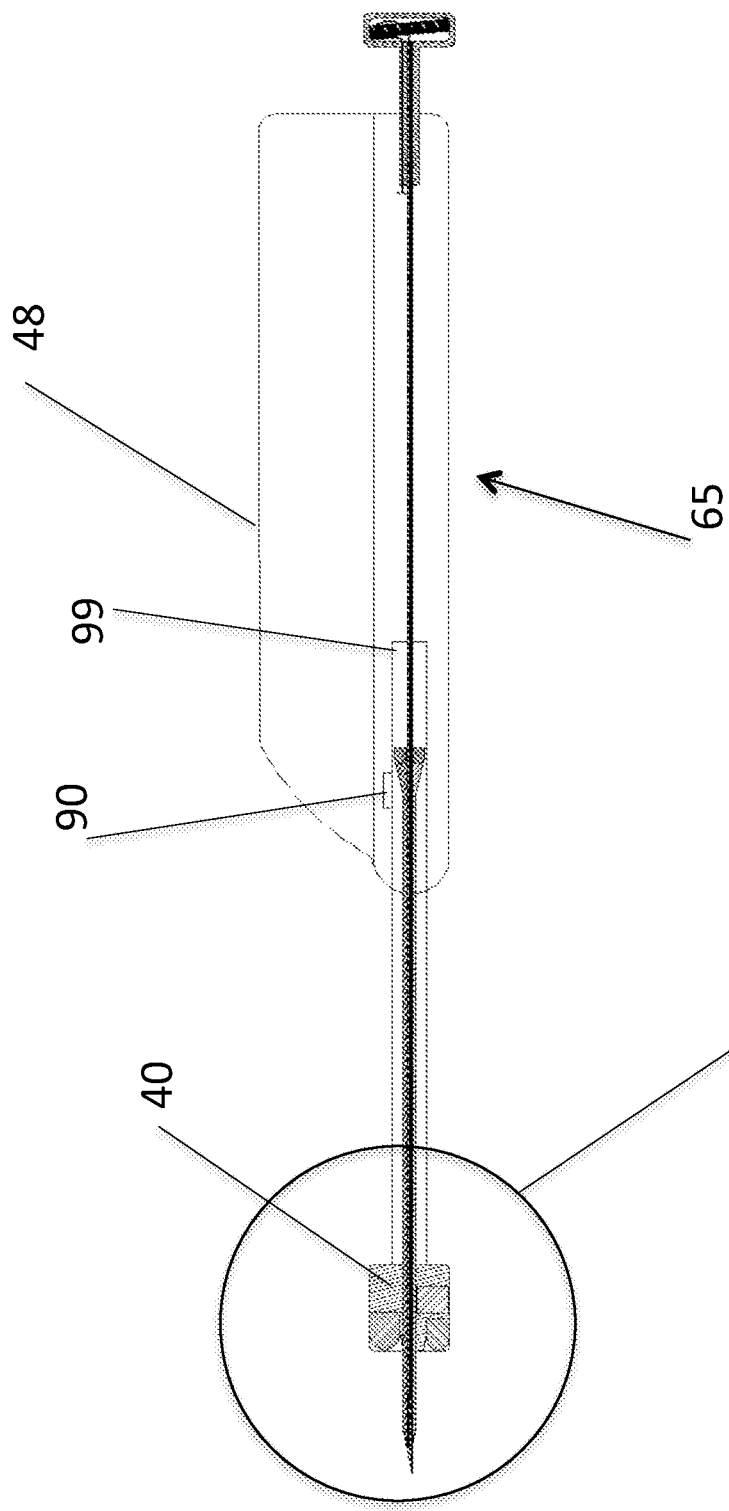
FIG. 26 is a section view of the deployment handheld with the holder partially retracted.

FIG. 26 is a section view of the deployment handheld with the holder partially retracted. The surgeon has pressed the pushrod release 48 to allow the holder 40 movement. The deployment assembly 65 has internal space to allow the pushrod end 99 clearance.

As the right pushrod 43 is retracted, the position would be sensed with a linear variable displacement transducer (LVDT) or pattern digital encoding means. This holder position sense information would be used by the microprocessor to correctly adjust the distance measurement to the marker clip 15.

Figure 27:
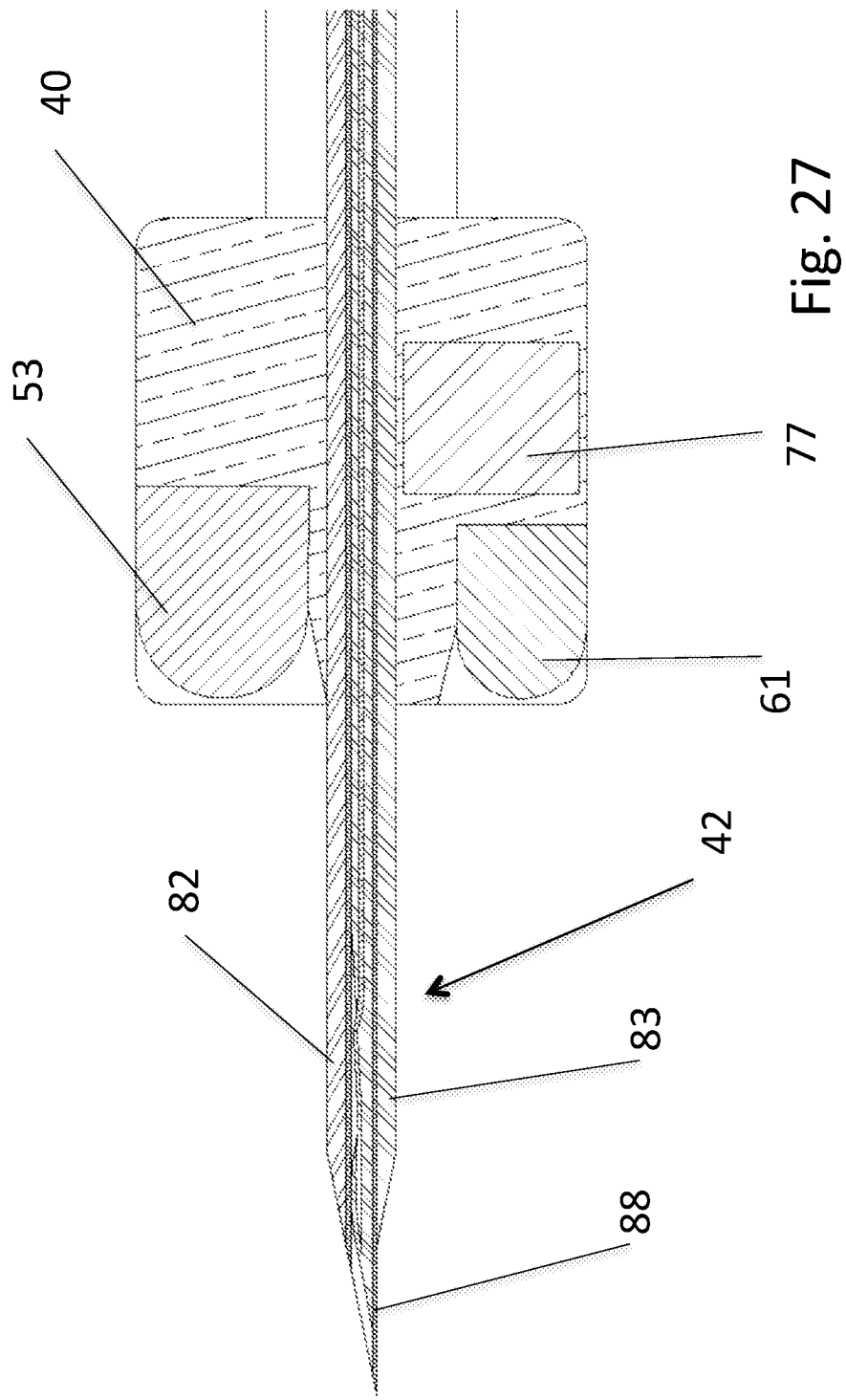
FIG. 27 is a close up section view of the holder taken from FIG. 26.

FIG. 27 is a close up section view of the holder taken from FIG. 26. This view shows the light pipes 82, 33 and needle 88 exposed with the holder 40 retracted. The light pipes 82,83, 89 and needle 88 are permanently attached to the deployment assembly 65.

Figure 28:
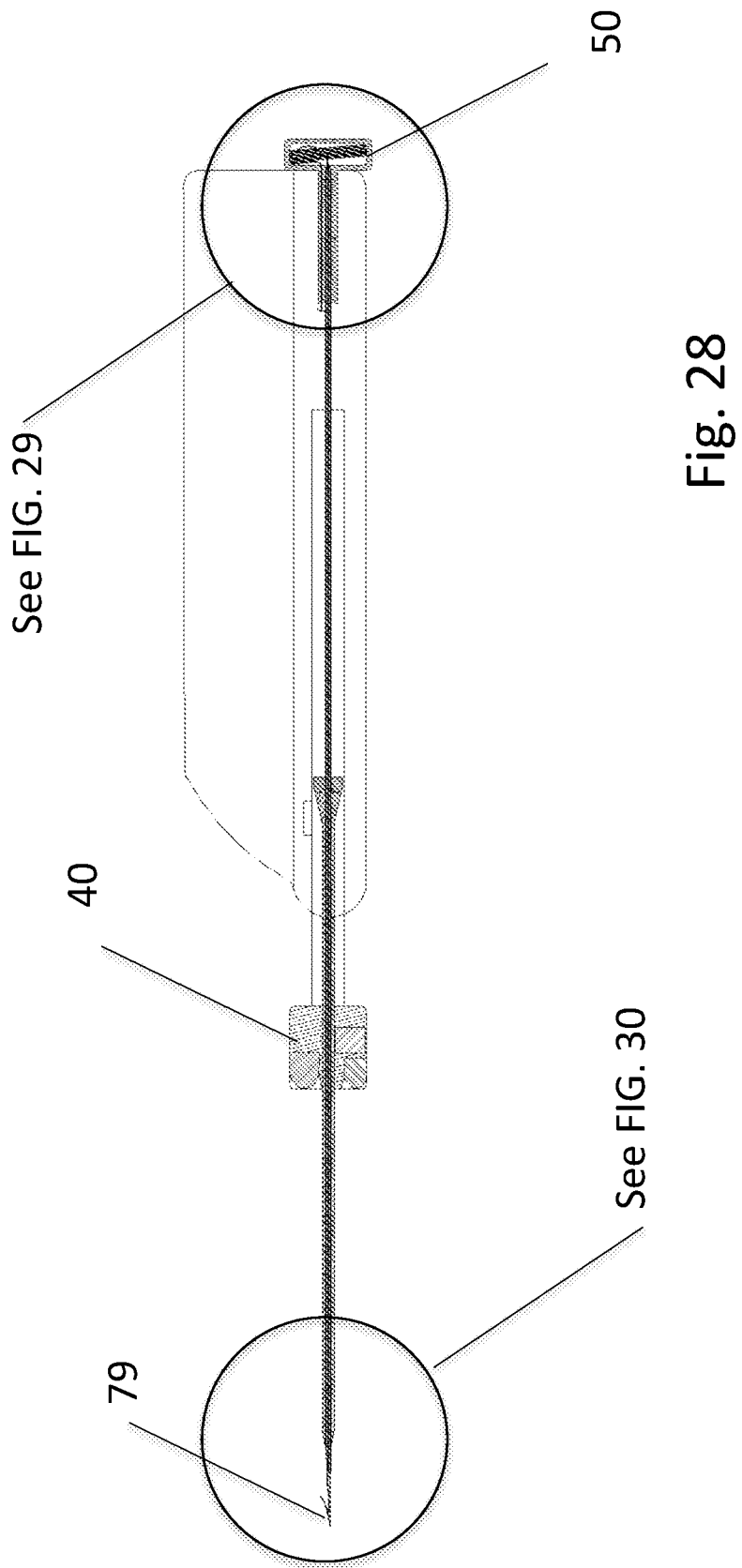
FIG. 28 is a section view of the deployment handheld with the button spool depressed.

FIG. 28 is a section view of the deployment handheld with the button spool depressed. Note that the holder 40 has been further retracted. This retraction would be the amount of distance from the surface of the breast 14 to the marker clip 15 location. The button spool 50 has been depressed resulting in the forward movement of the guide wire 79.

Figure 29:
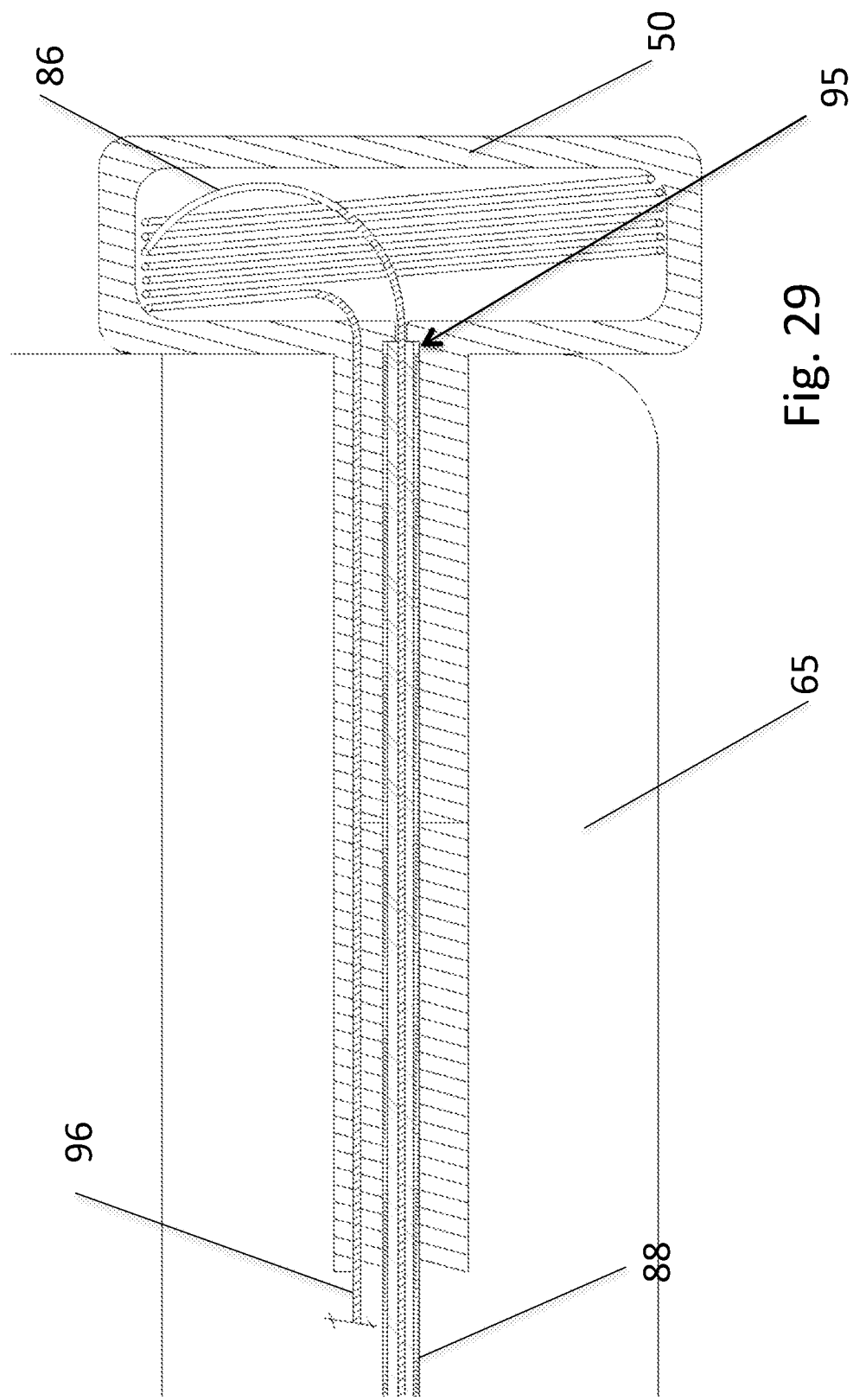
FIG. 29 is a close up section view of the button spool taken from FIG. 28.

FIG. 29 is a close up section view of the button spool taken from FIG. 28. The button spool 50 has been depressed until it comes in contact with the deployment assembly 65.

Figure 30:
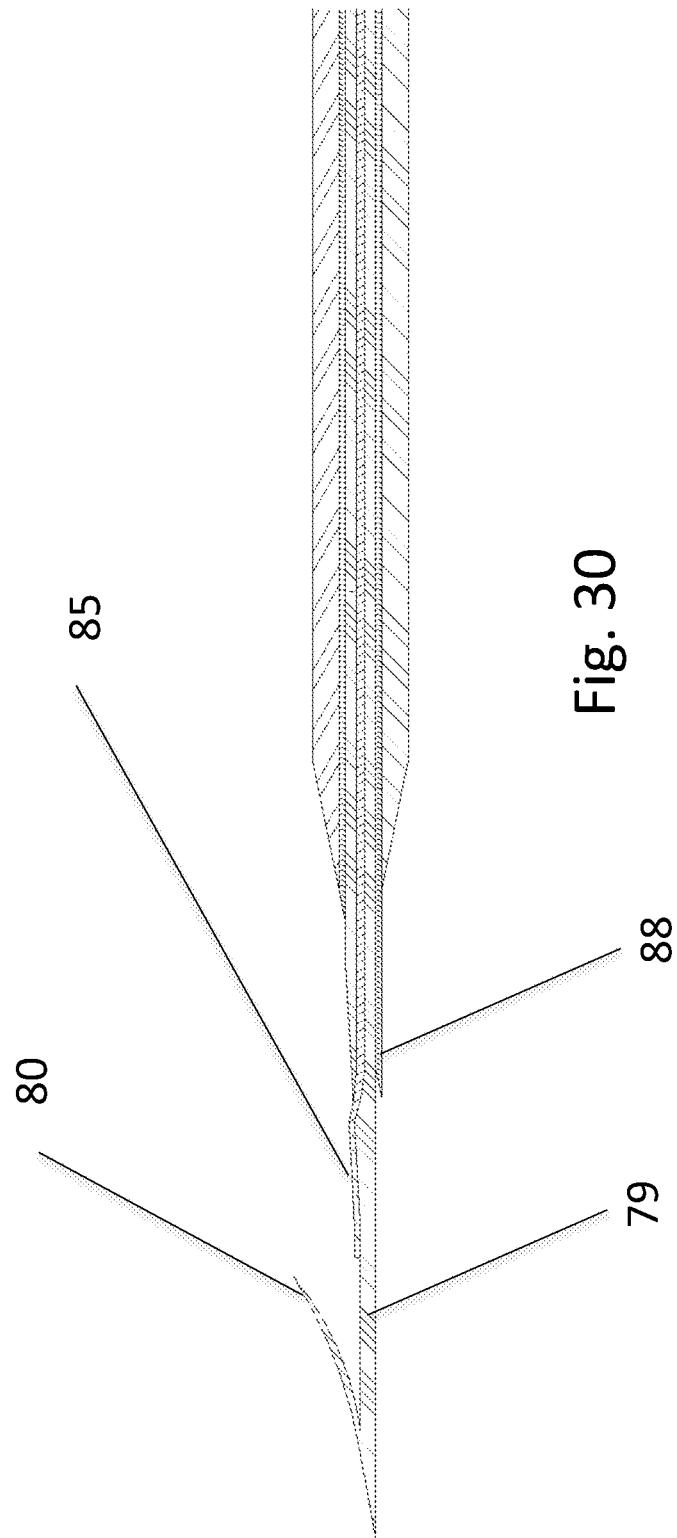
FIG. 30 is a close up section view of the guide wire tip taken from FIG. 28.

FIG. 30 is a close up section view of the guide wire tip taken from FIG. 28. The guide wire hook 80 is now in the deployed position. The extended guide wire hook 80 would engage the breast 14 tissue to resist backward movement of the guide wire 79. The next step in the procedure would be for the surgeon to pull the deployment assembly 65 backward causing the needle 88 to exit the breast 14. The guide wire 79 would slide within the needle 88. The ultrasonic wire 86 would unwind within the button spool 50 and extend into the needle 88. When the guide wire 79 has fully exited the needle 88, the final distance of the guide wire 79 to the marker clip can be checked with still functioning tip ultrasonic 85. The last step of the procedure would be to cut the ultrasonic wire 86 and tape the loose end of the guide wire 79 outside the breast 14.

Figure 31:
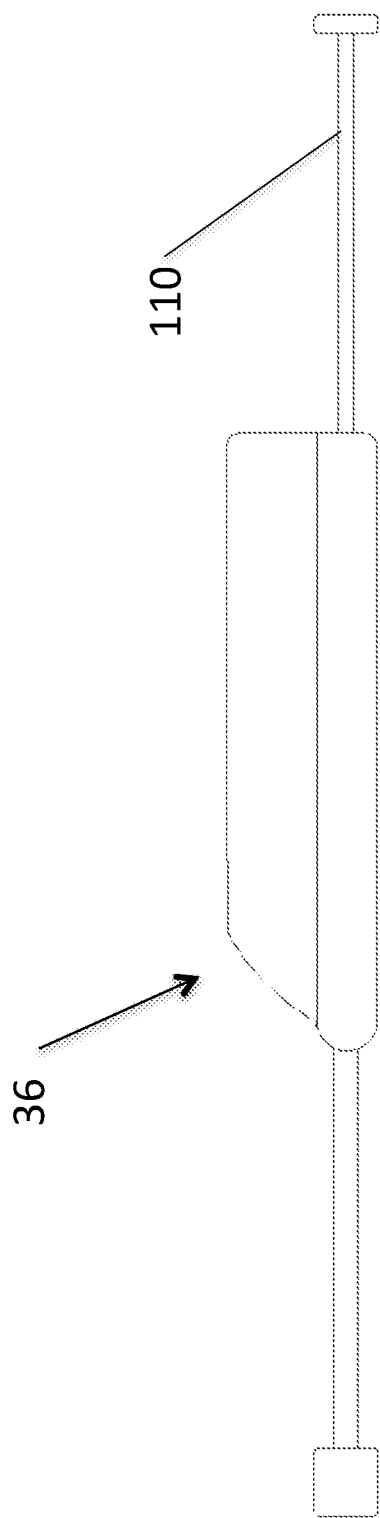
FIG. 31 is a side view of the deployment handheld with a extended button spool.

FIG. 31 is a side view of the deployment handheld with an extended button spool. This is an alternate construction to the button spool 50. The extended button spool 110 provides a pushing force on the guide wire 79 during the entire extraction of the needle 88 from the breast 14. This construction does not rely on the guide wire hook 80 pulling on the breast 14 tissue to cause guide wire 79 extraction from the needle 88.

Figure 32:
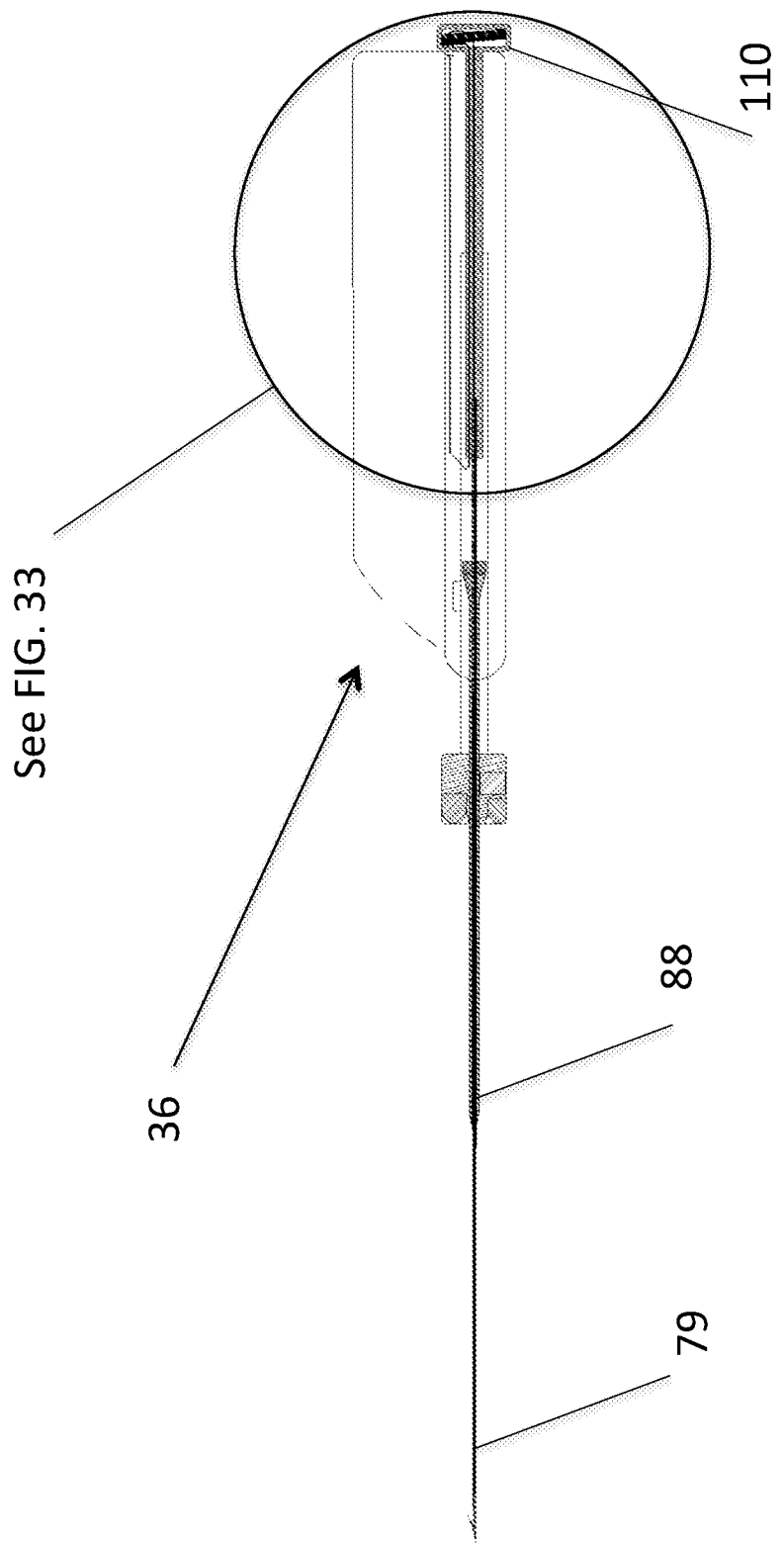
FIG. 32 is a modification of FIG. 28 with extended button spool.

FIG. 32 is a modification of FIG. 28 with extended button spool. This view is from the same section lines as FIG. 28 but with the alternate extended button spool 110 construction. Note from this view, the approximate 100 mm length of guide wire 79 exposed past the end of the needle 88. This length would provide full extraction of the needle 88 from the breast 14 and allow sufficient room for the surgeon to grasp the exposed guide wire 79. After grasping the exposed guide wire 79, the remainder of the guide wire 79 would be pulled through the needle 88 by continued retraction of the deployment handheld 36.

Figure 33:
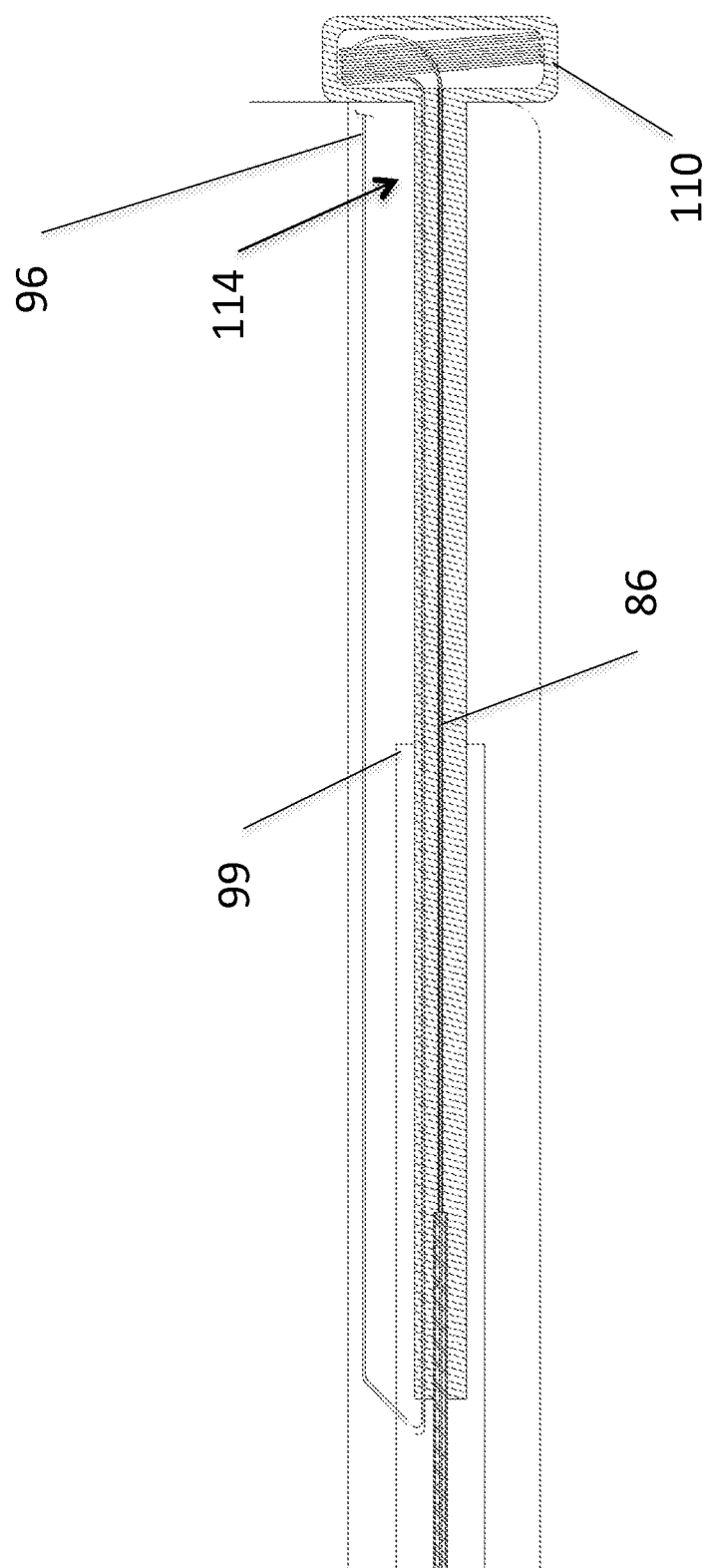
FIG. 33 is a close up section view of the extended button spool taken from FIG. 32.

FIG. 33 is a close up section view of the extended button spool taken from FIG. 32. Note the overlap of the pushrod end 99 and the extended button spool 110. The pushrods 41,43 would be relieved for this overlap distance to allow the extended button spool 110 movement.

A length of ultrasonic wire 86 would be coiled in the wire storage 114 area. This would allow the ultrasonic wire 86 to uncoil as the extended button spool 110 is depressed.

The operation of the deployment handheld 36 with the extended button spool 110 is as follows:
  a. The needle 88 is inserted into the breast 14 keeping the marker spot 68 centered. The distance from the tip ultrasonic 85 to the marker clip 15 would decrease as the needle 88 is inserted.
  b. The needle 88 insertion would be stopped when the distance indicates 5 mm.
  c. The extended button spool 110 would be slightly depressed while holding the deployment handheld 36 still. The distance from the tip ultrasonic 85 to the marker clip 15 would decrease as the extended button spool 110 is depressed.
  d. Depression of the extended button spool 110 would cease when the distance reaches zero or the distance begins to increase. The guide wire 79 is now in the optimal position.
  e. The surgeon would concurrently depress the extended button spool 110 while retracting the deployment handheld 36 in an attempt to not change the distance from the tip ultrasonic 85 to the marker clip 15.
  f. Motion (e) would continue until the needle 88 has exited the breast 14 and the guide wire 79 is exposed.
  g. The surgeon would grasp the exposed guide wire 79 and retract the deployment handheld 36 until the guide wire 79 completely exits the needle. As an alternate procedure, once sufficient guide wire 79 is exposed outside the breast; the guide wire could be cut. This would leave a portion of the guide wire 79 remaining in the needle 88.

In cases of extremely dense breast tissue or dense lesions marked by the marker clip 15, it may be impossible to advance the guide wire 79 past the needle 88. In such cases, the needle 88 would be advanced from +5 mm to zero. The guide wire 79 would then be kept stationary as the needle 88 is retracted. This could be done by holding firm pressure on the extended button spool 110 while simultaneously backing out the needle 88. The extended button spool 110 would depress at the same rate as the needle 88 is backing out thus keeping the guide wire 79 stationary.

Note that the optimal distance from tip ultrasonic 85 to the marker clip 15 is zero. To aid the surgeon, it is desirable for the guide wire 79 tip to be at the biopsy margin distance from the marker clip 15. If the desired biopsy margin distance is 10 mm, the tip ultrasonic 85 would be placed 10 mm from the guide wire 79 tip.

10 mm is a standard margin distance. If a larger margin distance is desired (such as 15 mm), the following two adjustments would be followed. In step (b), the insertion would be stopped when the distance indicates 0 mm. In step (d), depression of the extended button spool 110 would cease when the distance reaches 5 mm.

The preferred embodiment of the deployment handheld 36 includes the holder 40 LEDs 53-55, 60-62; and the extended button spool 110.

Figure 34:
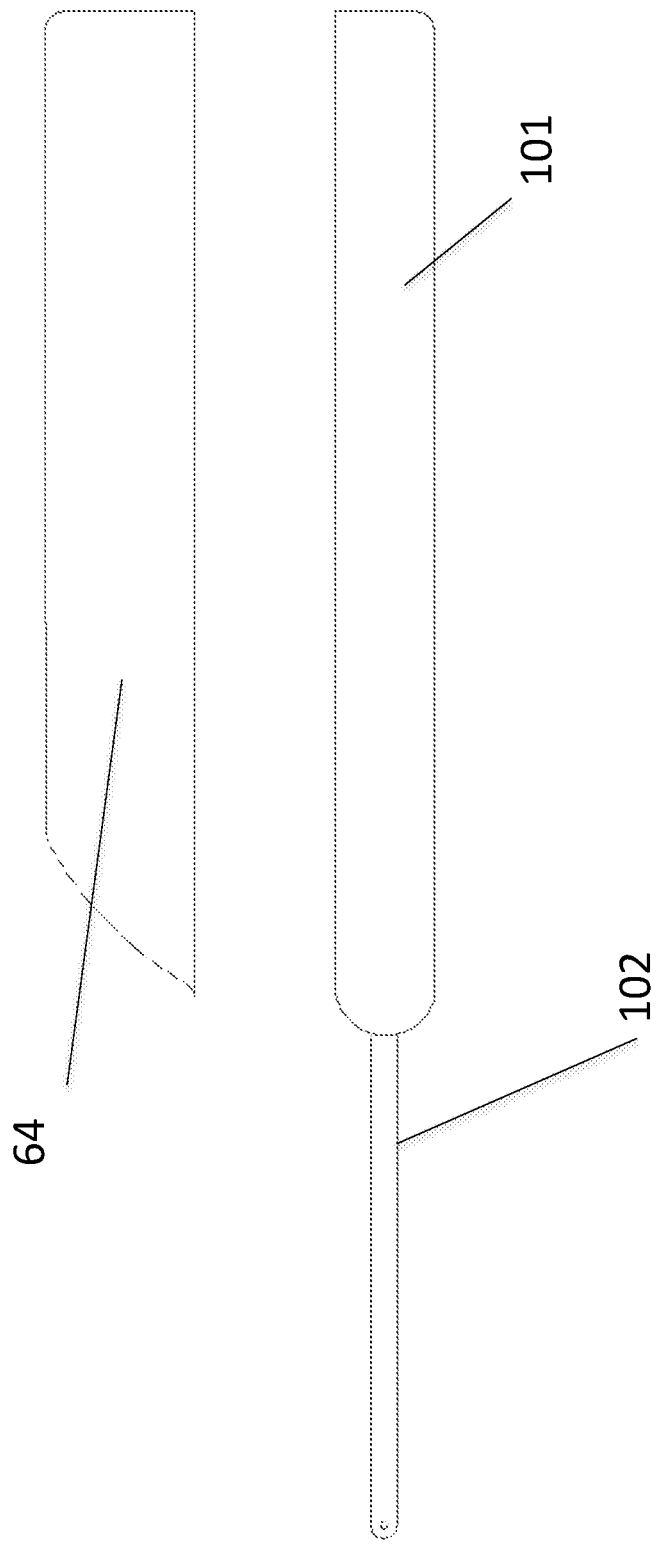
FIG. 34 is a side view of a separated clip distance handheld.

FIG. 34 is a side view of a separated distance handheld. After the placement of the guide wire 79, the upper handle 64 would be separated from the deployment assembly 65. The upper handle 64 would then be attached to the clip distance assembly 101. As long as the upper handle 64 has not been powered down, it will remain paired with the marker clip 15.

Figure 35:
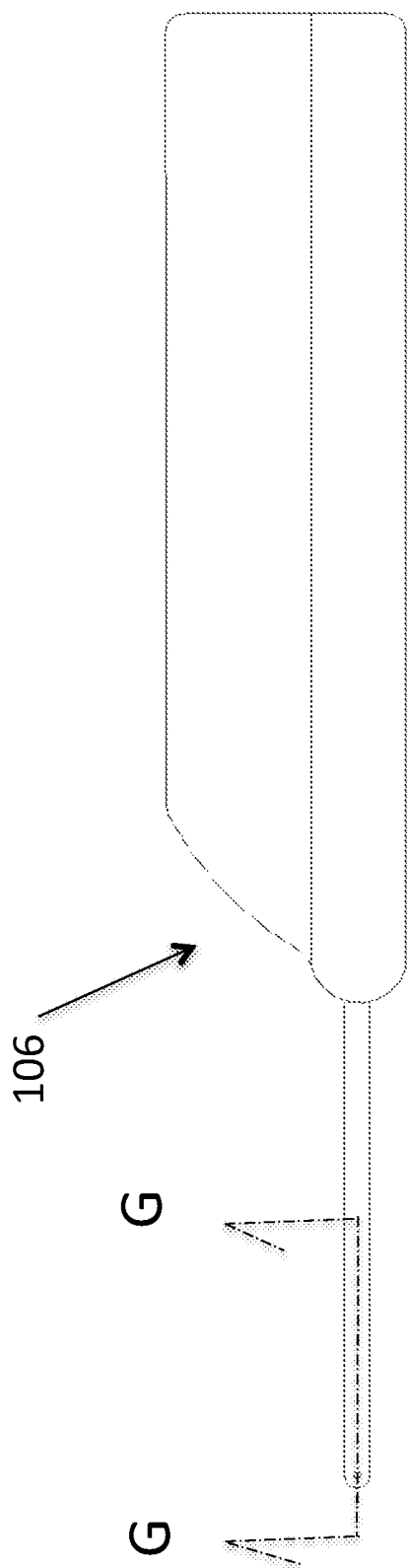
FIG. 35 is a side view of a clip distance handheld.

FIG. 35 is a side view of a distance handheld.

FIG. 36 is a close up section view of the distance handheld tip taken along section line G-G from FIG. 35. The probe 102 is permanently fixed to clip distance assembly 101. The probe ultrasonic 104, a piezoelectric ultrasonic emitter, is located near the end of the probe 102. The probe ultrasonic wires 120 are connected to the probe ultrasonic 104 and the clip distance assembly 101.

Several probe openings 122 are provided at the tip of the probe 102. These probe openings 122 are to allow air transmission of the ultrasonic sound in the case when the probe 102 is not in direct contact with breast 14 tissue or the specimen.

The function of the clip distance handheld 106 is to provide a readout of the distance from the marker clip 15 to the probe ultrasonic 104. It would use the same measurement methodology as the deployment handheld 36.

FIG. 37 is a close up section view of the clip distance handheld flexible tip. This section view is similar to FIG. 36 except the flexible probe 124 includes two flex joints 126.

FIG. 38 is a close up section view of the clip distance handheld flexible tip in a bent position. In this view one of the flex joints 126 has been manually bent approximately 85 degrees.

The surgeon would insert the clip distance handheld 106 into the surgical site to measure between the surgical specimen margin and the marker clip 15. The flex joints 126 could be molded to any angle to facilitate measuring precise margins on the lateral and deep aspects of the specimen. After the specimen has been removed, the clip distance handheld 106 could then be used to confirm margins and to confirm that the marker clip 15 that was localized was included in the specimen. This would eliminate the need for immediate radiographic evaluation and allow the surgeon to close the patient 12 immediately without waiting for a radiology interpretation.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawings and description in this disclosure are provided to help the reader understand the invention, and do not limit the scope of the claims.

The invention claimed is:

1. A guide wire deployment apparatus comprising:
  a) a handpiece comprising a power means, a digital processing means, a needle, and a guide wire;
  b) a marker clip comprising a second power means and a second digital processing means;
  c) a wireless digital communication means between the marker clip and the handpiece;
  d) a means for sensing an angular position of the marker clip relative to a longitudinal axis of the needle, wherein the means for sensing comprises a photocell affixed to the marker clip and a light emitter slideably connected to the needle;
  e) a second means for sensing a distance from a tip of the needle to the marker clip; and
  f) a means to push the guide wire out the tip of the needle.

2. The apparatus of claim 1 wherein the power means comprises a battery; and the second power means comprises a wireless power receiver with a capacitive storage.

3. The apparatus of claim 1 wherein the second means for sensing comprises a sonic sensor affixed to the marker clip and a sonic emitter slideably connected to the needle.

4. The apparatus of claim 2 wherein the second digital processing means comprises a circuit board and surface mount components.

5. The apparatus of claim 2 wherein the second digital processing means comprises die cut components and gold lead wires.

6. The apparatus of claim 1 wherein the marker clip further comprises a radiology opaque image bar.

7. A guide wire deployment apparatus comprising:
 a) a handpiece comprising a battery, a wireless power emitter, a digital processing means, a needle, and a guide wire;
 b) a marker clip comprising a wireless power receiver, a capacitor power supply, and a second digital processing means;
 c) a wireless communication means between the marker clip and the handpiece;
 d) a means for sensing an angular position of the marker clip relative to a longitudinal axis of the needle, wherein the means for sensing comprises a photocell affixed to the marker clip and a light emitter slideably connected to the needle;
 e) a second means for sensing a distance from a tip of the needle to the marker clip; and
 f) a means to push the guide wire out the tip of the needle.

8. The apparatus of claim 7 wherein the second means for sensing comprises a sonic sensor affixed to the marker clip and a sonic emitter slideably connected to the needle.

9. The apparatus of claim 7 wherein the second digital processing means comprises a circuit board and surface mount components.

10. The apparatus of claim 7 wherein the second digital processing means comprises die cut components and gold lead wires.

11. The apparatus of claim 8 wherein the marker clip further comprises a radiology opaque image bar.

12. The apparatus of claim 7 wherein the second means for sensing comprises a sonic sensor affixed to the marker clip and a sonic emitter affixed proximate to a tip of the guide wire.

13. The apparatus of claim 12 wherein the tip of the guide wire includes a hook, the hook is stored inside the tip of the needle and the hook extends when the guide wire is pushed out the tip of the needle.

14. The apparatus of claim 12 wherein the sonic sensor is connected to an ultrasonic wire, the ultrasonic wire is attached to the guide wire, and the ultrasonic wire is coiled to allow the guide wire movement relative to the needle.

15. The apparatus of claim 7 wherein the angular position comprises a magnitude and an angular orientation.

16. The apparatus of claim 7 wherein the means for sensing comprises a narrow light pattern means for sensing and a wide light pattern means for sensing.

17. The apparatus of claim 7 wherein the second means for sensing comprises a short range means for sensing and a pressed against the breast means for sensing.

18. A guide wire deployment apparatus comprising:
 a) a handpiece comprising a power means, a digital processing means, a needle, and a guide wire;
 b) a marker clip comprising a second power means and a second digital processing means;
 c) a wireless digital communication means between the marker clip and the handpiece;
 d) a means for sensing an angular position of the marker clip relative to a longitudinal axis of the needle, wherein the means for sensing comprises a photocell affixed to the marker clip and a light emitter affixed to a tip of the needle;
 e) a second means for sensing a distance from the tip of the needle to the marker clip; and
 f) a means to push the guide wire out the tip of the needle.

19. The apparatus of claim 18 wherein the second means for sensing comprises a sonic sensor affixed to the marker clip and a sonic emitter affixed proximate to a tip of the guide wire.

* * * * *